(12) United States Patent
Batra et al.

(10) Patent No.: US 9,233,121 B2
(45) Date of Patent: Jan. 12, 2016

(54) COMPOSITIONS AND METHODS FOR THE TREATMENT OF CANCER

(75) Inventors: Surinder K. Batra, Omaha, NE (US); Moorthy P. Ponnusamy, Omaha, NE (US)

(73) Assignee: BOARD OF REGENTS OF THE UNIVERSITY OF NEBRASKA, Omaha, NE (US)

( * ) Notice: Subject to any disclaimer, the term of this patent is extended or adjusted under 35 U.S.C. 154(b) by 0 days.

(21) Appl. No.: 13/984,411

(22) PCT Filed: Mar. 12, 2012

(86) PCT No.: PCT/US2012/028761
§ 371 (c)(1),
(2), (4) Date: Sep. 26, 2013

(87) PCT Pub. No.: WO2012/125554
PCT Pub. Date: Sep. 20, 2012

(65) Prior Publication Data
US 2014/0057962 A1   Feb. 27, 2014

Related U.S. Application Data

(60) Provisional application No. 61/451,715, filed on Mar. 11, 2011, provisional application No. 61/488,863, filed on May 23, 2011.

(51) Int. Cl.
| | |
|---|---|
| A61K 31/70 | (2006.01) |
| C07H 21/02 | (2006.01) |
| C07H 21/04 | (2006.01) |
| C12Q 1/68 | (2006.01) |
| A61K 31/713 | (2006.01) |
| C12N 15/113 | (2010.01) |
| A61K 31/7068 | (2006.01) |
| G01N 33/574 | (2006.01) |

(52) U.S. Cl.
CPC ........... *A61K 31/713* (2013.01); *A61K 31/7068* (2013.01); *C12N 15/113* (2013.01); *C12Q 1/6881* (2013.01); *C12Q 1/6886* (2013.01); *G01N 33/57496* (2013.01); *C12N 2310/14* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,932,442 A | 8/1999 | Lal et al. | |
| 6,680,196 B1 | 1/2004 | Batra et al. | |
| 2004/0259247 A1* | 12/2004 | Tuschl et al. | .................. 435/375 |
| 2009/0227533 A1 | 9/2009 | Bader et al. | |
| 2009/0297536 A1 | 12/2009 | Chin et al. | |
| 2010/0305188 A1 | 12/2010 | Nakano et al. | |

OTHER PUBLICATIONS

Ponnusamy, et al. "RNA Polymerase II associated factor 1/PD2 maintains self-renewal by its interaction with Oct3/4 in mouse embryonic stem cells." Stem Cells. Oct. 9, 2009;27: 3001-3011.

Moniaux, et al. "The human homologue of the RNA polymerase II-associated factor 1 (hPaf1), localized on the 19q13 amplicon, is associated with tumorgenesis." Oncogene. Feb. 20, 2006;25:3247-3257.

Dey, et al. "Human RNA Polymerase II-Association Factor 1 (hPaf1/PD2) Regulates Histone Methylation and Chromatin Remodeling in Pancreatic Cancer." PLoS One. Oct. 2011;6(10):e26926.

Batra, S.K., et al., "Isolation and Characterization of a Complementary DNA (PD-1) Differentially Expressed by Human Pancreatic Ductal Cell Tumors" (1991) Cell Growth & Differentiation 2:385-390.

Zhu, B., et al., "The Human PAF Complex Coordinates Transcription with Events Downstream of RNA Synthesis" (2005) Genes & Development 19:1668-1673.

* cited by examiner

*Primary Examiner* — Sean McGarry
(74) *Attorney, Agent, or Firm* — Robert C. Netter, Jr.; Dann, Dorfman, Herrell & Skillman

(57) ABSTRACT

Compositions and methods for treating, detecting, and diagnosing cancer are disclosed.

14 Claims, 26 Drawing Sheets

| Day 14 | 1000 cells | 5000 cells |
|---|---|---|
| SW1990_SP | 11 | 22 |
| SW1990_NSP | 5 | 8 |

```
  1 MAPTIQTQAQREDGHRPNSHRTLPERSGVVCRVKYCNSLPDIPFDPKFIT
 51 YPFDQNRFVQYKATSLEKQHKHDLLTEPDLGVTIDLINPDTYRIDPNVLL
101 DPADEKLLEEEIQAPTSSKRSQQHAKVVPWMRKTEYISTEFNRYGISNEK
151 PEVKIGVSVKQQFTEEEIYKDRDSQITAIEKTFEDAQKSISQHYSKPRVT
201 PVEVMPVFPDFKMWINPCAQVIFDSDPAPKDTSGAAALEMMSQAMIRGMM
251 DEEGNQFVAYFLPVEETLKKRKRDQEEEMDYAPDDVYDYKIAREYNWNVK
301 NKASKGYEENYFFIFREGDGVYYNELETRVRLSKRRAKAGVQSGTNALLV
351 VKHRDMNEKELEAQEARKAQLENHEPEEEEEEMETEEKEAGGSDEEQEK
401 GSSSEKEGSEDEHSGSESEREEGDRDEASDKSGSGEDESSEDEARAARDK
451 EEIFGSDADSEDDADSDDEDRGQAQGGSDNDSDSGSNGGGQRSRSHSRSA
501 SPFPSGSEHSAQEDGSEAAASDSSEADSDSD
```

Figure 10A

```
   1 ttctcgcccg cccacctcat ctcaacccac tttccgcggg gagcggcgcc aagctgggcc
  61 ttcctcggat caggcgtccc ctgaagtcgg cacgcccctc tgcgtccccc ttcggtcccg
 121 ctaggacccc gtccgggctg ccgtcgcctc gtcgctatgg cgcccaccat ccagacccag
 181 gcccagcggg aggatggcca caggcccaat tcccaccgga ctctgcctga gaggtctgga
 241 gtggtctgcc gagtcaagta ctgcaatagc ctccctgata tccccttcga ccccaagttc
 301 atcacctacc ccttcgacca gaacaggttc gtccagtaca aagccacttc cttggagaaa
 361 cagcacaaac atgacctcct gactgagcca gacctggggg tcaccatcga tctcatcaat
 421 cctgacacct accgcatcga ccccaatgtt cttctagatc cagctgatga gaaactttg
 481 gaagaggaga ttcaggcccc caccagctcc aagagatccc agcagcacgc gaaggtggtg
 541 ccatggatgc gaaagacaga gtacatctcc actgagttca accgttatgg catctccaat
 601 gagaagcctg aggtcaagat tggggtttct gtgaagcagc agtttaccga ggaagaaata
 661 tacaaagaca gggatagcca gatcacagcc attgagaaga cttttgagga tgcccagaaa
 721 tcaatctcac agcattacag caaaccccga gtcacaccgg tggaggtcat gcctgtcttc
 781 ccagactta agatgtggat caatccatgt gctcaggtga tctttgactc agacccagcc
 841 cccaaggaca cgagtggtgc agctgcgttg gagatgatgt ctcaggccat gattaggggc
 901 atgatggatg aggaagggaa ccagtttgtg gcctatttcc tgcctgtaga agagacgttg
 961 aagaaacgaa agcgggacca ggaggaggag atggactatg caccagatga tgtgtatgac
1021 tacaaaattg ctcggagta caactggaac gtgaagaaca agctagcaa gggctatgag
1081 gaaaactact tcttcatctt ccgagagggt gacggggttt actacaatga gttggaaacc
1141 agggtccgcc ttagtaagcg ccgggccaag gctggggttc agtcaggcac caacgccctg
1201 cttgtggtca acatcgggga catgaatgag aaggaactgg aagctcagga ggcacggaag
1261 gcccagctag aaaaccacga accggaggag gaagaggaag aggagatgga gacagaagag
1321 aaagaagctg ggggctcaga tgaggagcag gagaagggca gcagcagtga gaaggagggc
1381 agtgaagatg agcactcggg cagcgagagt gaacgggagg aaggtgacag ggacgaggcc
1441 agtgacaaga gtggcagtgg tgaggacgag agcagcgagg atgaggcccg ggctgcccgt
1501 gacaaagagg agatctttgg cagtgatgct gattctgagg acgatgccga ctctgatgat
1561 gaggacagag acaggcccca aggtggcagt gacaatgatt cagacagcgg cagcaatggg
1621 ggtggccagc ggagccggag ccacagccgc agcgccagtc ccttccccag tggcagcgag
1681 cactcggccc aggaggatgg cagtgaagct gcagcttctg attccagtga agctgatagt
1741 gacagtgact gagtcccagg gcattcaggg ctggttcaga caccattatt gtgagcagca
1801 aagcactttt ctagtggtct gtttgtgagc ctttcacttg tttgttcccc accccaaac
1861 ctttgctgtt aataaagtca acttctcttt aaaaaaaaaa aaaaaaaaaa aaaaaaaaaa
1921 aaaaaaaaaa aaaaaa
```

Figure 10B

COMPOSITIONS AND METHODS FOR THE TREATMENT OF CANCER

This application is a §371 application of PCT/US2012/028761, filed Mar. 12, 2012, which claims priority under 35 U.S.C. §119(e) to U.S. Provisional Patent Application No. 61/451,715, filed on Mar. 11, 2011 and U.S. Provisional Patent Application No. 61/488,863, filed on May 23, 2011. The foregoing applications are incorporated by reference herein.

FIELD OF THE INVENTION

The present invention relates to the field of cancer stem cells and its specific target to improve the cancer therapy. Specifically, the instant invention provides the novel cancer stem cell specific marker hPaf1/PD2 and provides its role in CSC maintenance along with novel targeted therapy for CSCs to manage all type of cancers.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

Stem cells having cancerous properties are widely known as cancer stem cells (CSCs) or fraction of the cancer cell population having stem like property are called CSC. These CSCs constitute a small proportion of tumor mass which are found to exist within many human tumors including colon (O'Brien et al. (2007) Nature 445:106-110), brain (Singh et al. (2004) Nature 432:396-401), breast (Al-Hajj et al. (2003) Proc. Natl. Acad. Sci., 100:3983-3988), prostate (Collins et al. (2005) Cancer Res., 65:10946-10951), pancreatic (Li et al. (2007) Cancer Res., 67:1030-1037) and ovarian cancers (Szotek et al. (2006) Proc. Natl. Acad. Sci., 103:11154-11159). Typically, CSCs possess the distinctive properties of regenerating tumors, promoting metastasis, causing aggressive cancers and most importantly they must be capable of self-renewal (Reya et al. (2001) Nature 414:105-111). Additionally, CSCs through their drug efflux mechanisms can make the tumor drug resistant. Hence failure to target this particular cell population has made the current therapeutic strategies inefficient and tumor recurrence is observed in most patients with advanced stage cancers even after treatment. Therefore, considerable research efforts have been directed towards the identification of specific cancer stem cell markers in different cancers for therapeutic targeting.

To date, only a few cancer stem cell markers like CD24, CD34, CD44, CD117, ESA and CD133 have been identified (Al-Hajj et al. (2003) Proc. Natl. Acad. Sci., 100:3983-3988; Ferrandina et al. (2008) Int. J. Gynecol. Cancer 18:506-514; Ma et al. (2007) Gastroenterology 132:2542-2556; O'Brien et al. (2007) Nature 445:106-110; Szotek et al. (2006) Proc. Natl. Acad. Sci., 103:11154-11159). CSCs have characteristic activation of self-renewal pathways such as Wnt, Shh and Notch signaling (Ivanova et al. (2006) Nature 442:533-538; Ponnusamy et al. (2008) J. Ovarian Res., 1:4; Reya et al. (2001) Nature 414:105-111). Cancer stem/initiating cells propagate the tumor and can account for cancer development, progression, metastasis and tumor relapse (Szotek et al. (2006) Proc. Natl. Acad. Sci., 103:11154-9). Identification of specific molecules that maintain CSCs and targeting these molecules provide an important tool to fight cancer.

SUMMARY OF THE INVENTION

In accordance with the instant invention, methods for inhibiting, treating, and/or preventing cancer in a subject are provided. In a particular embodiment, the method comprises administering at least one human polymerase associated factor/pancreatic differentiation 2 (hPaf1/PD2) antagonist and at least one chemotherapeutic agent to the subject. In a particular embodiment, the cancer is a drug resistant cancer, particularly one resistant to the chemotherapeutic agent to be administered to the subject. The hPaf1/PD2 antagonist may decrease the expression of hPaf1/PD2 or hPaf1/PD2 encoding nucleic acids or may decrease the activity of hPaf1/PD2. In a particular embodiment, the hPaf1/PD2 antagonist is an inhibitory nucleic acid molecule such as an antisense molecule, siRNA, and shRNA.

In accordance with another aspect of the instant invention, methods of detecting and/or identifying cancer stem cells are provided. In a particular embodiment, the method comprises detecting or measuring the expression of hPaf1/PD2 or hPaf1/PD2 encoding nucleic acids, wherein cells that over-express hPaf1/PD2 or hPaf1/PD2 encoding nucleic acids compared to other (e.g., control) cells are cancer stem cells. The methods may further comprise detecting or measuring at least one other cancer stem cell marker and/or at least one self-renewal marker.

The instant invention also provides methods of diagnosing a subject as having an increased risk for cancer, particularly an aggressive, metastatic, or drug-resistant cancer. In a particular embodiment, the method comprises detecting or measuring the expression of hPaf1/PD2 or hPaf1/PD2 encoding nucleic acids in a biological sample obtained from the subject, wherein over-expression of hPaf1/PD2 or hPaf1/PD2 encoding nucleic acids compared to a normal biological sample (e.g., normal or healthy tissue or non-aggressive, non-metastatic, or non-drug-resistant cancer) is indicative of the increased risk for cancer.

In accordance with the instant invention, therapeutic compositions are also provided. In a particular embodiment, the composition comprises at least one hPaf1/PD2 antagonist, at least one chemotherapeutic agent, and at least one pharmaceutically acceptable carrier. Kits comprising a first composition comprising at least one hPaf1/PD2 antagonist and at least one pharmaceutically acceptable carrier, and a second composition comprising at least one chemotherapeutic agent and at least one pharmaceutically acceptable carrier, are also provided herein.

BRIEF DESCRIPTION OF THE DRAWINGS

FIG. 4 shows the expression of hPaf1/PD2 and CSC markers. SP and NSP cells were processed for protein extraction and western blotting using standard procedures.

FIG. 8 shows the knockdown of hPaf1/PD2 with drug treatment in SP cells.

FIG. 10A provides an amino acid sequence of human polymerase associated factor (hPaf1)/pancreatic differentiation 2 (PD2) (hPaf1/PD2) (SEQ ID NO: 2). FIG. 10B provides the nucleotide sequence of an mRNA sequence encoding hPaf1/PD2 (SEQ ID NO: 3). Underlined nucleotides indicate the coding region (SEQ ID NO: 4).

DETAILED DESCRIPTION OF THE INVENTION

Figure 1A:
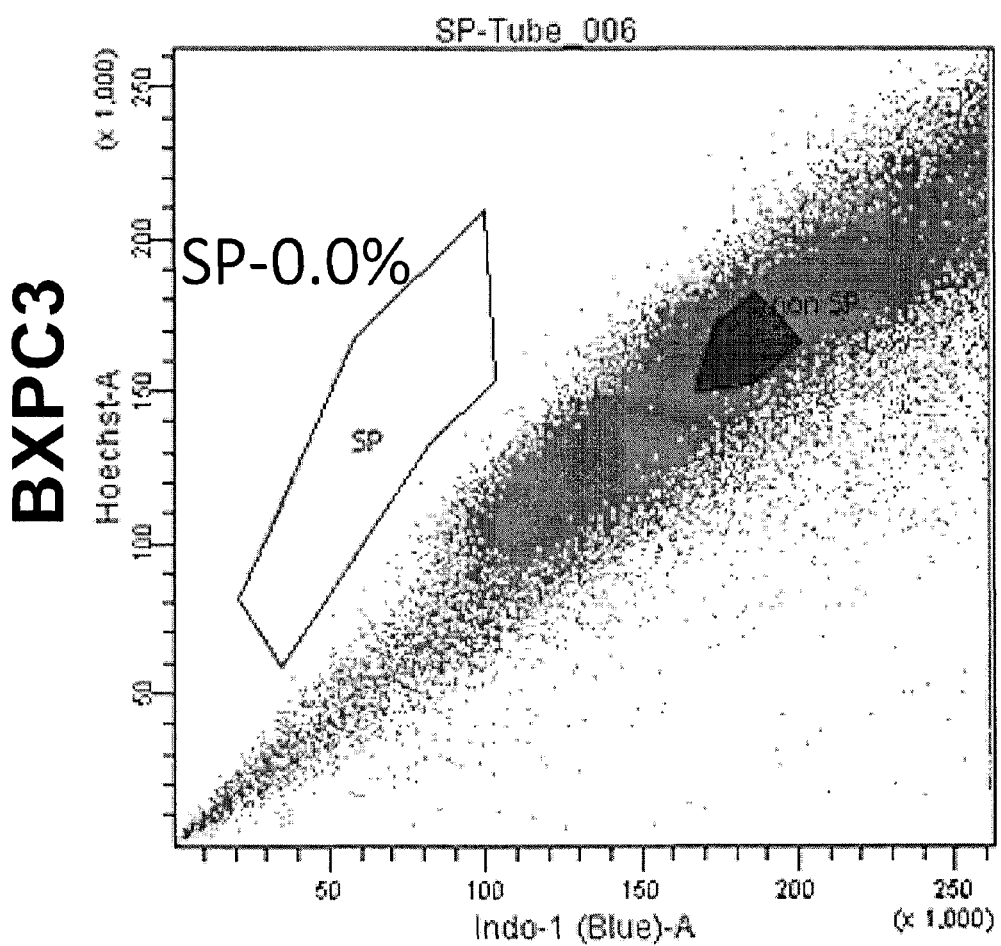
FIG. 1 provides an analysis of side population (SP) and non-side population (NSP) cells in Hoechst 33342 dye in pancreatic cancer cells. The SP cells from pancreatic cancer cells (BXPC3—0.0%, MiaPaCa—0.0% and SW1990—0.2%) were sorted by FACS analysis (FIGS. 1A-1C). SW1990—0.2% SP cells were isolated and maintained in stem cell specific condition. In parallel, verapamil, an agent that reverses the multidrug resistance was used to ensure that the isolated cells were purely SP cells (FIG. 1D).

Human polymerase associated factor (hPaf1)/pancreatic differentiation 2 (PD2) functions as a key regulator of self-renewal in mouse embryonic stem cells (mESC) (Ponnusamy et al. (2009) Stem Cells 27:3001-3011). The involvement of hPaf1/PD2 in the maintenance of self-renewal of mESCs is via its interaction with Oct3/4 (Ponnusamy et al. (2009) Stem Cells 27:3001-3011). A novel pancreatic differentiation 2 (PD2) gene (GenBank Accession number AJ401156) has been identified in the 19q13.2 amplicon in pancreatic cancer cells via differential screening analysis (Moniaux et al. (2006) Oncogene 25:3247-3257). Later, it was discovered that PD2 is the human homologue of the yeast RNA polymerase II-associated factor 1 (yPaf1) and is part of the human PAF (hPAF) complex which consists of other subunits namely hLeo1, hCtr9, parafibromin/Cdc73, and hSki8 (Moniaux et al. (2006) Oncogene 25:3247-3257; Zhu et al. (2005) Genes Dev., 19:1668-1673). Overexpression of hPaf1/PD2 in poorly differentiated pancreatic cancer (PC) cells compared to well differentiated PC cells was observed due to gene amplification in the 19q13 locus (Moniaux et al. (2006) Oncogene 25:3247-3257). In parallel, it was observed that the overexpression of this gene in the immortalized NIH3T3 cell line led to the oncogenic transformation of the cells (Moniaux et al. (2006) Oncogene 25:3247-3257).

Cancer stem cells (CSC) or side population (SP) is a subset of the cancer cell population which is responsible for the aggressiveness of the disease, tumorigenicity, metastasis and drug resistance leading to tumor relapse in the patients. Identification of a novel CSC maintenance marker and targeting it therefore will therefore improve the efficiency of treatment. It has been shown that hPaf1/PD2 (PD2 is the human homologue of the yeast RNA polymerase II-associated factor 1) plays a major role in the maintenance of self-renewal process in mouse embryonic stem cells (mESC). It is shown herein that the side population (SP) isolated from SW1990 (pancreatic cancer cell line) and OVCAR3 (ovarian cancer cell line) showed a cobblestone appearance (in stem cell specific condition) characteristic of the cancer stem cell phenotype. In addition, the tumorsphere assay also shows larger spheres in SP cells compared to that of the non-side population (NSP) cells. The in vivo tumorigenicity assay shows significant tumor growth in mice subcutaneously injected with SP cells from SW1990 cells whereas very small to no tumor was observed in case of the NSP cell injected mice. Interestingly, the expression of hPaf1/PD2 was significantly higher in SP cells when compared to NSP cells. Likewise, the expression of CSC markers like ALDH1 and CD133 were elevated in SP than in NSP. Self-renewal markers Oct3/4, Shh, β-catenin and Twist also showed increased expression in SP cells compared to NSP cells. Furthermore, gemcitabine treatment of SP-SW1990 cells led to increased viability and enrichment of the SP cell population. However, knockdown of hPaf1/PD2 in SP cells followed by gemcitabine treatment decreased both the viability of cells and the expression of CD133 and multi drug resistant gene 2 (MDR2). Overall, the results indicate a novel role of hPaf1/PD2 in the maintenance of cancer stem cell population as well as in drug resistance.

Herein, the role of hPaf1/PD2 in cancer stem cells, particularly pancreatic and ovarian cancer stem cells, was investigated. These CSCs isolated using Hoechst dye (through its drug efflux property) were confirmed via both in vitro tumorsphere assays and in vivo animal model assays. There are many well-established models to demonstrate the isolation of cancer stem cells from different cancer cells using Hoechst dye and surface markers (Al-Hajj et al. (2003) Proc. Natl. Acad. Sci., 100:3983-3988; Collins et al. (2005) Cancer Res., 65:10946-10951; Dalerba et al. (2007) Annu. Rev. Med., 58: 267-284; Dean et al. (2005) Nat. Rev. Cancer 5:275-284; Engelmann et al. (2008) Cancer Res., 68:2419-2426; Ferrandina et al. (2008) Int. J. Gynecol. Cancer 18:506-514; Marsden et al. (2009) Methods Mol. Biol., 590:363-375; Mimeault et al. (2007) J. Cell Mol. Med., 11:981-1011; Ponnusamy et al. (2008) J. Ovarian Res., 1:4; Szotek et al. (2006) Proc. Natl. Acad. Sci., 103:11154-11159). By performing the in vitro tumorsphere assays the SP cells (5000 cells) display larger tumorspheres compared to smaller tumorspheres induced by 5000 NSP cells. Formation of spherical colonies was reported to be a property characteristic of stem/progenitor cells and verifies a high developmental and proliferative potency of SP cells (Engelmann et al. (2008) Cancer Res., 68:2419-2426). High tumorigenic potential is the hallmark of CSCs. Similarly, the in vivo animal model assays show larger tumors in mice with 5000 SP cells implanted both subcutaneously and orthotopically compared to small tumors or complete absence of tumors in mice with 5000 NSP cells injected. The results of both in vitro and in vivo assays indicates that SP cells are highly more potent than NSP cells.

hPaf1/PD2 is a newly discovered self-renewal stem cell factor in mouse embryonic stem (ES) cells (Ponnusamy et al. (2009) Stem Cells 27:3001-3011). It has been shown that it is involved in self-renewal by interacting with ES cell marker Oct3/4 (Ponnusamy et al. (2009) Stem Cells 27:3001-3011). It is well established that self-renewal is a common and important property of all types of stem cells including CSCs (Dalerba et al. (2007) Annu. Rev. Med., 58:267-284; Ponnusamy et al. (2008) J. Ovarian Res., 1:4; Reya et al. (2001) Nature 414:105-111). Similarly, it has been shown that knockdown of PAF complex proteins alter the ES cell fate (Ding et al. (2009) Cell Stem Cell 4:403-415). In addition, it has been shown that hPaf1/PD2 is significantly overexpressed in poorly differentiated pancreatic cancer cells compared to well-differentiated cells (Moniaux et al. (2006) Oncogene 25:3247-3257). In the present study, the expression of hPaf1/PD2 was correlated with the maintenance of cancer stem cell population isolated from pancreatic and ovarian cancer cells. The expression of hPaf1/PD2 in SP and NSP cells was investigated and was found that hPaf1/PD2 was significantly enriched in SP of both pancreatic and ovarian cancer cells. Further the analysis of stem cell specific markers (ALDH1, CD133 and CD44) was correlated with hPaf1/PD2 expression indicating that isolated SP cells maintain the cancer stem-like characters and hPaf1/PD2 is involved in the maintenance of cancer stem cell population. In addition, the analysis of self-renewal markers Oct3/4, Shh and Twist showing increased level of expression in isolated SP cells compared to NSP cells along with hPaf1/PD2 indicates that this molecule is involved in the self-renewal process of CSCs.

Understanding the underlying mechanism of drug resistance and tumor relapse with the regulation and expression of different genes in cancer stem cells leads to effective mechanisms for combating CSCs based drug resistance in different cancers. It has been reported that in cancer patients chemotherapy increases $CD44^+CD24^-$/low cancer cells owing to the chemoresistance of cancer initiating cells (Zhou et al. (2009) Nat. Rev. Drug Discov., 8:806-823). Gemcitabine treated SP cells survived till 20 days in contrast to the NSP cells, indicating that the isolated SP population retained their drug resistance property. The expression of hPaf1/PD2 was also maintained in SP cells during the period of drug treatment along with ALDH1, a drug resistant and cancer stem cell specific marker. This indicates that hPaf1/PD2 is also involved in the process of drug resistance in cancer stem cell population. It was then investigating whether change of hPaf1/PD2 expression affects chemoresistance of cancer stem cells. Interestingly, silencing of hPaf1/PD2 led to cell death of the SP population on gemcitabine treatment indicating that the loss of hPaf1/PD2 compromises the drug resistance property of CSCs. Loss of mRNA expression of other markers such as CD133, MDR2 along with hPaf1/PD2 confirms that hPaf1/PD2 is involved in the maintenance of cancer stem cell population and imparts drug resistance.

Figure 9:
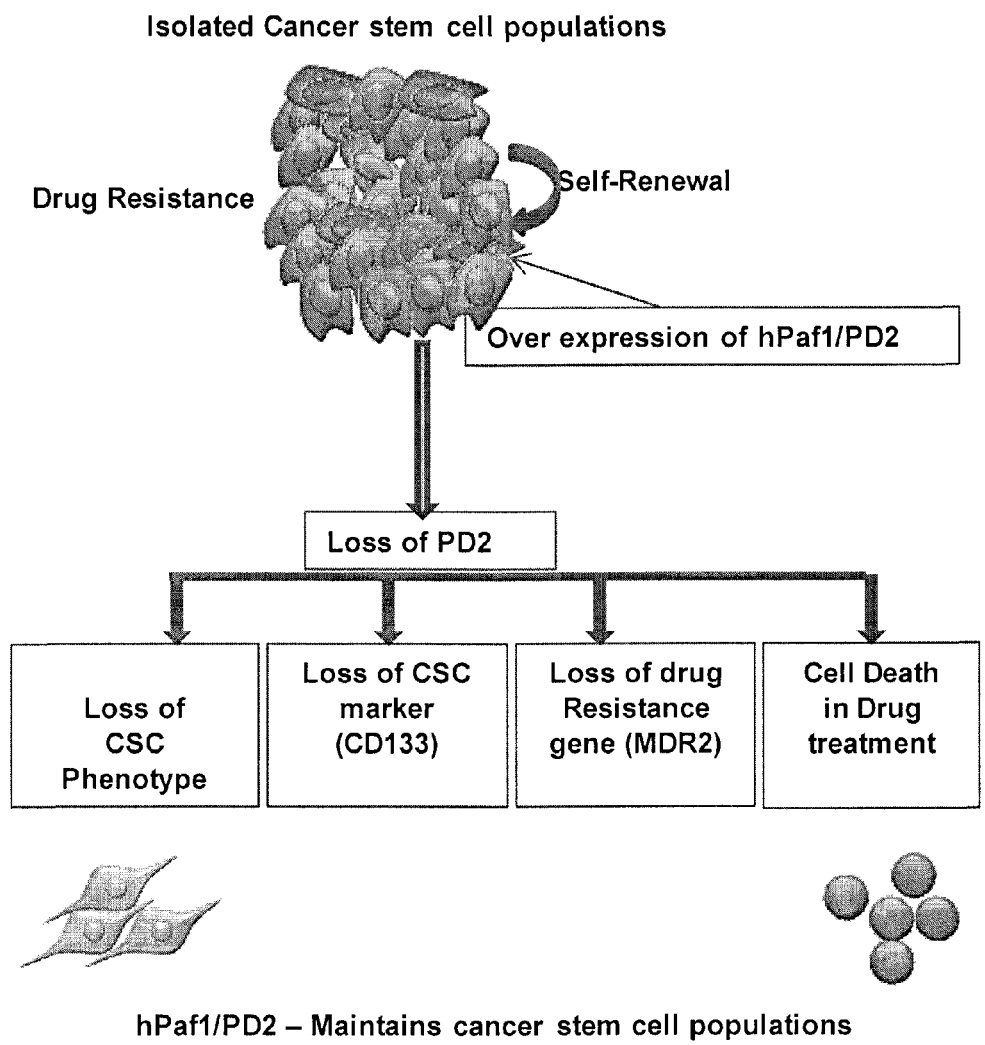
FIG. 9 provides a schematic illustration for the role of hPaf1/PD2 in CSCs. The isolated cancer stem cells express hPaf1/PD2 and maintain the self-renewal and drug resistance property. The knockdown of hPaf1/PD2 in CSCs with drug treatment reduces the viability of SP cells. Furthermore, its inhibition changed the CSC phenotype, reduced the CD133 and MDR2 gene of SP cells. Overall, the diagram demonstrates the role of hPaf1/PD2 in the maintenance of drug resistance.

Herein, the role of hPaf1/PD2 in cancer, particularly the SP cells of pancreatic and ovarian cancers, is demonstrated. The SP maintains tumorigenesis and drug resistance properties along with enriched expression of hPaf1/PD2 and other cancer stem cell specific markers (ALDH1, CD133 and CD44) and self-renewal markers (Oct3/4, Shh and Twist). Furthermore, the inhibition of hPaf1/PD2 leads to loss of CSC phenotype and drug resistance property (FIG. 9). Although other CSC markers exist, hPaf1/PD2 stands out as a novel marker due to its ability to maintain the self-renewal property and the cellular morphology of cancer stem cells. This was evident via the drug resistance and drug sensitivity in the presence and absence of hPaf1/PD2 respectively. Overall, the results provided herein indicate that hPaf1/PD2 plays an important role in the maintenance of cancer stem cells and is also involved in drug resistance by either directly or indirectly controlling the MDR2 gene (FIG. 9). More importantly, the identification of cancer stem cells with specific maintenance marker hPaf1/PD2 provides critical information for developing novel therapeutic strategies to reduce the incidence of tumor recurrence in cancer patients.

Methods of Treatment

In accordance with the instant invention, compositions and methods for inhibiting (e.g., reducing or slowing), treating, and/or preventing cancer in a subject are provided. In a particular embodiment, the methods comprise administering to a subject in need thereof at least one hPaf1/PD2 antagonist which decreases the expression and/or activity of hPaf1/PD2. As stated hereinabove, GenBank Accession No. AJ401156 provides the nucleotide and amino acid sequences of hPaf1/PD2. The sequences are also provided in FIG. 10. In a particular embodiment, the cancer is pancreatic, ovarian, breast, brain, lung, or prostate cancer. In a particular embodiment, the cancer is pancreatic or ovarian cancer.

hPaf1/PD2 antagonists of the instant invention may disrupt the function or activity of hPaf1/PD2 and/or decrease expression of hPaf1/PD2. In a particular embodiment, the hPaf1/PD2 antagonist is an inhibitory nucleic acid molecule (e.g., antisense, siRNA, or shRNA). The inhibitory nucleic acid molecule may inhibit hPaf1/PD2 via RNA interference. In a particular embodiment, the inhibitory nucleic acid molecule comprises a sequence which is at least 90%, at least 95%, or 100% homologous or complementary with a nucleic acid molecule encoding hPaf1/PD2. In a particular embodiment, the hPaf1/PD2 has an amino acid sequence at least 80%, at least 85%, at least 90%, at least 95%, at least 97%, at least 99%, or 100% homologous (identical) to SEQ ID NO: 2. The inhibitory nucleic acid molecule may comprise a sequence which is at least 90%, at least 95%, or 100% homologous or complementary with SEQ ID NO: 3 or SEQ ID NO: 4. In a particular embodiment, the inhibitory nucleic acid molecule is an siRNA molecule comprising SEQ ID NO: 1. In a particular embodiment, the siRNA molecule comprises 5'-CAG-GUUCGUCCAGUACAAA-3' (SEQ ID NO: 5). The hPaf1/PD2 antagonist may also be a protein, polypeptide, antibody or fragment thereof, or small molecule inhibitor of hPaf1/PD2.

The inhibitory nucleic acid molecules of the instant invention may be delivered to the subject either naked or in modified form. For example, the inhibitory nucleic acid molecules of the instant invention may be stabilized by modifying the nucleic acid backbone. The in vivo stability of siRNAs may be increased by chemically modifying the RNA backbone with, without limitation, 2' F, 2'O-Me, and/or 2' H substitutions in the RNA backbone (Behlke (2006) Molec. Ther. 13: 644-670; Aagaard et al. (2007) Adv. Drug Deliv. Rev., 59:75-86). The inhibitory nucleic acid molecules may also be conjugated to polymers or cholesterol for in vivo stability. The inhibitory nucleic acid molecules may also be encompassed in liposomes (e.g., cationic liposomes) or nanoparticles.

In a particular embodiment of the instant invention, vectors encoding the inhibitory nucleic acid molecule are delivered to the subject. For example, DNA based expression vectors may be used to express shRNAs or separate sense and antisense strands of an siRNA (e.g., from the same or different promoters). In a particular embodiment, the vectors comprise a Pol II or Pol III promoter for expressing the inhibitory nucleic acid molecule. In a particular embodiment, the inhibitory nucleic acid molecules are delivered to a subject via a viral vector. Viral vectors include, without limitation, adenoviral vectors, adeno-associated virus-(AAV) vectors, and retroviral vectors (e.g., lentiviral vectors; murine leukemia virus (MLV), human immunodeficiency virus (HIV), feline immunodeficiency virus (FIV), and equine infectious anemia virus (EIAV).

The methods of the instant invention also encompass the administration of at least one chemotherapeutic agent with the at least one hPaf1/PD2 antagonist. The chemotherapeutic agent may be administered sequentially and/or concurrently with the hPaf1/PD2 antagonist. For example, a chemotherapeutic agent may be administered before, after, and/or at the same time as the administration of a hPaf1/PD2 antagonist. In a particular embodiment, the hPaf1/PD2 antagonist is administered at least prior to the chemotherapeutic agent.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diphtheria toxin, Pseudomonas exotoxin, and others listed above; thereby generating an immunotoxin when conjugated or fused to an antibody); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase I inhibitor (e.g., topotecan); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate); pyrimidine antagonists (analogs) such as fluorouracil (5-fluorouracil), gemcitabine, fluorodeoxyuridine, CB3717, azacitidine, cytarabine, and floxuridine; purine antagonists (analogs) such as mercaptopurine, 6-thioguanine, fludarabine, pentostatin; asparginase; ribonucleotide reductase inhibitors (such as hydroxyurea); tubulin interactive agents (e.g., vincristine, vinblastine, docetaxel, and paclitaxel (Taxol®)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); immunomodulator (e.g., levamisole); and antihormonal antigens (e.g., tamoxifen, antiandrogen agents such as flutamide; and antiadrenal agents such as mitotane and aminoglutethimide). In a particular embodiment, the chemotherapeutic agent is selected from the group consisting of cisplatin, gemcitabine, doxorubicin, 5-fluoruracil, cyclophosphamide, dactinomycin, levamisole, etoposide, topotecan, thiotepa, vinblastine, paclitaxel, and docetaxel.

As demonstrated herein, the delivery of an hPaf1/PD2 antagonist to a drug resistant cancer renders the cancer susceptible at least to the drug to which it was previously resistant. Accordingly, the instant invention encompasses methods of inhibiting, treating, and/or preventing a drug resistant cancer in a subject. The methods comprise administering to a subject in need thereof at least one hPaf1/PD2 antagonist as described hereinabove and at least one chemotherapeutic agent. In a particular embodiment, the chemotherapeutic agent is the chemotherapeutic agent to which the cancer was resistant prior to the administration of the hPaf1/PD2 antagonist. As stated hereinabove, the chemotherapeutic agent may be administered sequentially and/or concurrently with the hPaf1/PD2 antagonist. In a particular embodiment, the hPaf1/PD2 antagonist is administered at least prior to the chemotherapeutic agent.

Compositions comprising at least one hPaf1/PD2 antagonist, at least one chemotherapeutic agent, and at least one pharmaceutically acceptable carrier are encompassed by the instant invention. As explain hereinabove, such compositions may be administered, in a therapeutically effective amount, to a patient in need thereof for the treatment of cancer. Alternatively, the chemotherapeutic agent may be contained within a first composition with at least one pharmaceutically acceptable carrier and the hPaf1/PD2 antagonist may be contained within a second composition with at least one pharmaceutically acceptable carrier. Having the agents in separate compositions allows for ease of sequential and/or simultaneous administration. The instant invention also encompasses kits comprising at least one composition comprising at least one hPaf1/PD2 antagonist and at least one composition comprising at least one chemotherapeutic agent.

The agents and compositions of the present invention can be administered by any suitable route, for example, by injection (e.g., for local (direct, including to or within a tumor) or systemic administration), oral, pulmonary, topical, nasal or other modes of administration. The composition may be administered by any suitable means, including intratumoral, parenteral, intramuscular, intravenous, intraarterial, intraperitoneal, subcutaneous, topical, inhalatory, transdermal, intrapulmonary, intraarterial, intrarectal, intramuscular, and intranasal administration. In a particular embodiment, the composition is administered directly to the skin. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, Pa. Lippincott Williams & Wilkins. 2005. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Selection of a suitable pharmaceutical preparation depends upon the method of administration chosen. For example, the molecules of the invention may be administered by direct injection into any cancerous tissue or into the area surrounding the cancer. In this instance, a pharmaceutical preparation comprises the molecules dispersed in a medium that is compatible with the cancerous tissue.

As stated hereinabove, agents of the instant invention may also be administered parenterally by intravenous injection into the blood stream, or by subcutaneous, intramuscular, intratumor, intrathecal, or intraperitoneal injection. Pharmaceutical preparations for parenteral injection are known in the art. If parenteral injection is selected as a method for administering the molecules, steps should be taken to ensure that sufficient amounts of the molecules reach their target cells to exert a biological effect. The lipophilicity of the molecules, or the pharmaceutical preparation in which they are delivered, may have to be increased so that the molecules can arrive at their target locations. Methods for increasing the lipophilicity of a molecule are known in the art.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, topical, or parenteral. In preparing the molecule in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard chemotherapies. The dosage units of the molecules may be determined individually or in combination with each chemotherapy according to greater shrinkage and/or reduced growth rate of tumors.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Methods of Detection

In accordance with the instant invention, methods for identifying, detecting and/or isolating cancer stem cells are provided. In a particular embodiment, the method comprises detecting the presence or over-expression of hPaf1/PD2 (nucleic acids and/or protein) in a population of cells, wherein cells expressing or over-expressing hPaf1/PD2 are the cancer stem cells. The method may further comprise isolating the hPaf1/PD2 expressing cancer stem cells (e.g., via FACS). Method of detecting and/or measuring hPaf1/PD2 encoding nucleic acid molecules or hPaf1/PD2 proteins are described below.

In accordance with the present invention, methods of detecting cancer and/or an increased risk for cancer, particularly an aggressive, metastatic, and/or drug resistant cancer, in a subject are provided. Methods of diagnosing and/or prognosing cancer in a subject are also provided. The cancer may be detected in vivo (e.g., imaged) or in vitro. In a particular embodiment, the method comprises obtaining a biological sample from the subject and determining whether hPaf1/PD2 encoding nucleic acids and/or the hPaf1/PD2 protein is overexpressed and/or over active in the biological sample, wherein the presence of increased activity of hPaf1/PD2 or increased levels of hPaf1/PD2 encoding nucleic acids and/or the hPaf1/PD2 protein is indicative of cancer in the subject and/or indicative of an increased risk of metastasis, recurrence, and/or death. In a particular embodiment of the instant invention, the method comprises measuring hPaf1/PD2 encoding nucleic acids in the cells of the biological sample, wherein an increase in hPaf1/PD2 encoding nucleic acids in the biological sample compared to the biological sample obtained from a normal (healthy) subject is indicative of cancer in the subject (particularly an aggressive, metastatic, and/or drug resistant cancer) and/or indicative of an increased risk of metastasis, recurrence, and/or death. The biological sample may include biopsies of various tissues including, without limitation: pancreatic and ovarian tissue. Cellular examples of biological samples include tumor cells, ovarian cells, and pancreatic cells.

The ability to measure the amount of a nucleic acid molecule or protein in a sample are well known in the art and include, without limitation, PCR (e.g., real time PCR; e.g., with hPaf1/PD2 specific primers), hybridization techniques (e.g., with hPaf1/PD2 specific probes (probes which specifically bind hPaf1/PD2 to the exclusion of other nucleic acids); e.g., microarrays, Southern, Northern), and immunological techniques (e.g., using antibodies immunologically specific for hPaf1/PD2; immunoprecipitations, radioimmunoassays, enzyme-linked immunosorbent assays (ELISA), immunohistochemical assays, Western blot and the like). The antibodies may be conjugated, without limitation, to at least one detectable agent. Detectable agents include, for example, chemiluminescent moieties, bioluminescent moieties, fluorescent moieties, enzymes (e.g., horseradish peroxidase), contrast agents, radionuclides, isotopes (e.g., radioisotopes (e.g., $^3$H (tritium) and $^{14}$C) or stable isotopes (e.g., $^2$H (deuterium), $^{11}$C, $^{13}$C, $^{17}$O and $^{18}$O), optical agents for imaging, and metals (e.g., gold). In an alternative method, a secondary antibody which can recognize the hPaf1/PD2 antibody may be conjugated with the agents described above instead of with the hPaf1/PD2 antibody molecules. Contrast agents include, without limitation, metals (e.g., gold, gold particles or gold nanoparticles), paramagnetic or superparamagnetic ions for detection by MRI imaging and optical and fluorescence agents. Paramagnetic ions include, without limitation, Gd(III), Eu(III), Dy(III), Pr(III), Pa(IV), Mn(II), Cr(III), Co(III), Fe(III), Cu(II), Ni(II), Ti(III), and V(IV). Fluorescent agents include, without limitation, fluorescein and rhodamine and their derivatives. Optical agents include, without limitation, derivatives of phorphyrins, anthraquinones, anthrapyrazoles, perylenequinones, xanthenes, cyanines, acridines, phenoxazines and phenothiazines. In a particular embodiment, the method comprises incubating a biological sample with at least one antibody of the instant invention, optionally comprising at least one detectable label. Radioisotopes also include, without limitation, positron-emitting isotopes and alpha-, beta-, gamma-, Auger- and low energy electron-emitters. The radioisotopes include, without limitation: $^{13}$N, $^{18}$F, $^{32}$P, $^{33}$P, $^{64}$Cu, $^{66}$Ga, $^{67}$Ga, $^{68}$Ga, $^{67}$Cu, $^{77}$Br, $^{80m}$Br, $^{82}$Rb, $^{86}$Y, $^{89}$Zr, $^{90}$Y, $^{95}$Ru, $^{97}$Ru, $^{99m}$TC, $^{103}$Ru, $^{105}$Ru, $^{111}$In, $^{113m}$In, $^{121m}$Te, $^{122m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$In, $^{186}$Re, $^{186}$Re, $^{195m}$Hg, $^{211}$At, $^{212}$Bi, $^{213}$Bi, and $^{225}$Ac. When the conjugated antibodies of the instant invention are employed for radio-immunodetection, the radioisotope may be a gamma-emitting isotope. When the conjugated antibodies of the instant invention are employed for detection by ImmunoPET (positron emission tomography), the radioisotope may be a positron-emitting isotope such as, without limitation, $^{13}$N, $^{18}$F, $^{89}$Zr, $^{82}$Rb.

The above methods for identifying, diagnosing, or prognosing cancer (particularly an aggressive, metastatic, and/or drug resistant cancer) in a patient may further comprise detecting at least one other cancer stem cell marker (e.g., a nucleic acid or protein differentially expressed (e.g., increased or decreased) or having differential activity in cancer stem cells compared to other cancer cells) and/or at least one self-renewal marker (e.g., Oct3/4, Shh and Twist) in the biological sample. Examples of cancer stem cell markers include without limitation, CD34 (cluster of differentiation 24), CD117, CD133, CD44, CD24, ESA (epithelial surface antigen), and ALDH1 (aldehyde dehydrogenase isoform 1).

As stated hereinabove, the instant methods may be used to diagnose (e.g., determine an increased risk of) cancer in patient. The methods may also determine the prognosis of a patient, including stage and grade (particularly whether it is metastatic) of a tumor and its potential sensitivity to therapy (e.g., resistance to a chemotherapeutic agent). Similarly, the methods may be used to determine the efficacy of a treatment of a patient (e.g., which chemotherapeutic agent may be effective and/or whether to administer a hPaf1/PD2 antagonist). The loss or decrease of hPaf1/PD2 expression in a patient, particularly one undergoing treatment, over time may be indicative of remission (i.e., successful treatment), while the lack of change in hPaf1/PD2 levels in a patient undergoing treatment may be indicative of resistance to the therapy and may indicate that a different therapeutic strategy could be employed. Similarly, the gain of hPaf1/PD2 expression in a patient over time can be indicative of recurrence.

DEFINITIONS

As used herein, the term "cancer stem cell" refers to an undifferentiated cancer cell which is capable of 1) proliferation without substantially differentiation, giving rise to more progenitor cells and 2) differentiation to a more specialized or differentiated phenotype. In other words, "cancer stem cells" are cancer cells found within tumors that possess characteristics associated with normal stem cells—such as the ability to give rise to all cell types found in a particular cancer. Cancer stem cells are tumorigenic and can generate tumors through the stem cell processes of self-renewal and differentiation into multiple cell types. Cancer stem cells persist in tumors as a distinct population and contribute to relapse and/or metastasis. Typically, cancer stem cells possess at least one or more, if not all, of the following properties: 1) regenerate tumors, 2) promote metastasis, 3) cause aggressive cancers, 4) capable of self-renewal, 5) form spherical colonies, and 6) display tumor drug resistance.

As used herein, an "aggressive cancer" refers to a cancer that invades, metastasizes to distant organ sites, and/or grows fast.

As used herein, the term "drug resistant cancer" refers to a cancer that is resistant to one or more chemotherapeutic agents. Drug resistant tumors are characterized by a resumption of their growth and/or reappearance after having seemingly gone into remission, despite the administration of the chemotherapeutic agent, even with increasing dosage. Cancers that have developed resistance to two or more anti-cancer drugs are said to be "multi-drug resistant."

The term "metastatic cancer" refers to cancer that has spread from one part of the body to another.

As used herein, the terms "host," "subject," and "patient" refer to any animal, including humans.

As used herein, a "biological sample" refers to a sample of biological material obtained from a subject, preferably a human subject, including a tissue, a tissue sample, a cell sample, a tumor sample, and a biological fluid, e.g., blood or urine. A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy and an endoscopic biopsy.

As used herein, "diagnose" refers to detecting and identifying a disease in a subject. The term may also encompass assessing or evaluating the disease status (progression, regression, stabilization, response to treatment, etc.) in a patient known to have the disease.

As used herein, the term "prognosis" refers to providing information regarding the impact of the presence of cancer (e.g., as determined by the diagnostic methods of the present invention) on a subject's future health (e.g., expected morbidity or mortality, the likelihood of getting cancer and/or recurrence, drug resistance status of the cancer, and the risk of metastasis). In other words, the term "prognosis" refers to providing a prediction of the probable course and outcome of a cancer or the likelihood of recovery from the cancer.

As used herein, the term "prevent" refers to the prophylactic treatment of a subject who is at risk of developing a condition (e.g., cancer or metastatic cancer) resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a cancer results in at least a reduction in the size of a tumor and/or reduction in the number or size of metastases.

The phrase "effective amount" refers to that amount of therapeutic agent that results in an improvement in the patient's condition. A "therapeutically effective amount" of a compound or a pharmaceutical composition refers to an amount effective to prevent, inhibit, treat, or lessen the symptoms of a particular disorder or disease.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

Antisense molecules are oligonucleotides that hybridize under physiological conditions to a particular gene or to an mRNA transcript of such gene and, thereby, inhibit the transcription of such gene and/or the translation of such mRNA. The antisense molecules are designed so as to interfere with transcription or translation of a target gene upon hybridization with the target gene or its mRNA. Antisense molecules are typically between about 12 and about 50 nucleotides, particularly about 15 and about 30 nucleotides, but the exact length of the antisense oligonucleotide and its degree of complementarity with its target depend upon the specific target selected. The antisense molecule may be at least 95%, particularly 100%, complementary with the target sequence. An antisense oligonucleotide is preferably constructed to bind selectively with the target nucleic acid under physiological conditions. Antisense molecules may span the translational start site of mRNA molecules. Antisense constructs may also be generated which contain the entire gene sequence in reverse orientation. Antisense oligonucleotides targeted to any known nucleotide sequence can be prepared by oligonucleotide synthesis according to standard methods.

The term "siRNA" refers to small inhibitory RNA duplexes such as those that induce the RNA interference (RNAi) pathway. siRNA may vary in length, but are generally about 12 to about 35, about 20 to about 30, or about 21 nucleotides in length (see, e.g., Ausubel et al., eds., Current Protocols in Molecular Biology, John Wiley and Sons, Inc.). siRNA may have unpaired overhanging bases on the 5' or 3' end of the sense strand and/or the antisense strand. As used herein, the term "siRNA" includes duplexes of two separate strands and single strand molecules that can form hairpin structures comprising a duplex region (shRNA). For example, the shRNA may comprise the sense strand and antisense strand connected via a linker (e.g., about 3 to about 20, particularly about 4 to about 10 nucleotides). Methods of identifying targets sequences for an siRNA are available in the art (see, e.g., Invitrogen at www.invitrogen.com/sirna).

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, the oligonucleotide probe typically contains about 10 to about 100, about 10 to about 50, about 15 to about 30, about 15 to about 25, or about 20 to about 50, or more nucleotides. The probes herein may be selected to be complementary to different strands of a particular target nucleic acid sequence. The probes are preferably sufficiently complementary so as to be able to "specifically hybridize" or anneal with their respective target strands under a set of pre-determined conditions. Therefore, the probe sequence need not reflect the exact complementary sequence of the target, although they may. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically. In a particular embodiment, oligonucleotide probe may be at least 95%, particularly 100%, complementary with the target sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, the oligonucleotide primer is typically about 10 to about 25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. The primer may be at least 95%, particularly 100%, complementary with the target sequence.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "isolated" may refer to protein, nucleic acid, compound, or cell that has been sufficiently separated from the environment with which it would naturally be associated (e.g., so as to exist in "substantially pure" form). "Isolated" does not necessarily mean the exclusion of artificial or synthetic mixtures with other compounds or materials, or the presence of impurities that do not interfere with the fundamental activity, and that may be present, for example, due to incomplete purification.

The term "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

The phrase "operably linked," as used herein, may refer to a nucleic acid or amino acid sequence placed into a functional relationship with another nucleic acid or amino acid sequence. Examples of nucleic acid sequences that may be operably linked include, without limitation, promoters, cleavage sites, purification tags, transcription terminators, enhancers or activators and heterologous genes which when transcribed and translated will produce a functional product such as a protein, ribozyme or RNA molecule. The term "conjugated" refers to the joining by covalent or noncovalent means of two compounds or agents.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The following example is provided to illustrate various embodiments of the present invention. The example is illustrative and is not intended to limit the invention in any way.

EXAMPLE

Experimental Procedures

Isolation of Side Population (SP) and Non-Side Population (NSP) from Cancer Cell Lines To determine whether pancreatic and ovarian cancer cell lines contain candidate cancer stem cells, Hoechst 33342 (capacity to efflux the fluorescent DNA-binding dye) has been used to sort the SP by flow sorting. The SP and NSP cells from human pancreatic (PC) (SW1990, BXPC3 and MiaPaCa) and ovarian (OC) (OVCAR3, A2780 and 2008) cancer cells have been analyzed using Hoechst 33342 dye staining and performed flow-sorting (Szotek et al. (2006) Proc. Natl. Acad. Sci., 103:11154-11159) in SW1900 and OVCAR3 cells only. SP cells can actively pump-out the Hoechst 33342 dye and hence exhibit low fluorescence as compared to the non-SP cells. In parallel, verapamil—an agent that reverses the multidrug resistance—was used to ensure that the isolated cells were purely SP cells.

Cancer Stem Cell Culture

Both SP and NSP cells were cultured in gelatinized tissue culture dishes in stem cell specific medium containing Dulbecco's Modified Eagle's Medium (DMEM; GIBCO) and F12 supplemented with 10% ES specific fetal bovine serum (FBS; Invitrogen), L-glutamine (GIBCO), 100 nM nonessential amino acids (GIBCO), 1000 U/ml LIF (Sigma), bFGF (Invitrogen) and Pen/Strp. Two different conditions were maintained for both SP and NSP cells. First, both SP and NSP cells were maintained in the above-mentioned stem cell specific media and in another condition both the cells were maintained for a few days in 10% FBS containing DMEM media which was replaced with stem cell specific medium. The SP cells have also been grown in stem cell specific media and NSP cells have been grown in 10% FBS containing DMEM media. The NSP cells did not grow well in stem cell specific condition in higher passages but grew well in DMEM condition. Hence, NSP and SP cells were grown in both DMEM and stem-cell specific medium to isolate RNA and protein for further processing.

Tumorsphere Assay for Both SP and NSP Cells

Sphere clusters have been found to be highly tumorigenic and were able to propagate and reconstitute original tumor architecture when injected into permissive hosts. SP and NSP cells were suspended at a low density of 1000-5000 cells/well in six-well ultra-low attachment plate with stem cell specific media. On the 14$^{th}$ day of culture, spheres were viewed under the inverted phase-contrast microscope and were counted and photographed.

In Vivo Tumor Growth of SP and NSP Cells

To test the tumorigenic capacity, sorted SP and NSP cells from SW1990 were injected in low number (5000 cells with matrigel) subcutaneously in the dorsal fat pad of immuno-compromised nude mice (SP cells on the right side and NSP cells on the left side of each of the two animals). Tumor growth was observed after the 25$^{th}$ day and animals were sacrificed after 7 weeks. Furthermore, two animals each were used for the pancreatic orthotopic implantation with 1000 cells of both NSP and SP cell type. After 6 weeks of pancreatic orthotopic implantation animals were sacrificed and tumors were measured.

RNA Isolation and RT-PCR

Total cellular RNA was extracted from SP and NSP cells using the RNAeasy kit (Qiagen) and processed for reverse transcription. The initial PCR activation step was at 94° C. for four minutes, followed by the denaturation step at 94° C. for one minute, primer-annealing step at 58° C. for 30 seconds, extension step at 72° C. for one minute, and the final extension step at 72° C. for ten minutes. PCR reaction products were then separated by electrophoresis using a 2% agarose gel. Gels were stained using 0.5 mg/ml of ethidium bromide and illuminated with UV light. The GAPDH was used as a control gene.

RNA Interference

The human hPaf1/PD2 region was targeted with specific siRNA (sequence 5'-AACAGGUUCGUCCAGUACAAA-3'; SEQ ID NO: 1). Synthetic sense and antisense oligonucleotides (Dharmacon, Lafayette, Colo.) were annealed in 100 mM potassium acetate, 30 mM HEPES-KOH (pH 7.4), and 2 mM magnesium acetate for one minute at 90° C. and one hour at 37° C., and frozen. Oligonucleotides were transfected into cells with TransIT-TKO (Mirus, Madison, Wis.) in accordance with the supplier's recommendations. Gemcitabine (6 µM) treatment was done for 20 days.

Immunoblot Assay

SP and NSP cells were processed for protein extraction and western blotting using standard procedures. Briefly, the cells were washed twice in PBS and lysed in RIPA buffer (100 mM Tris, 5 mM EDTA, 5% NP40; pH8.0) containing protease inhibitors (1 mM phenyl-methyl sulphonyl fluoride, 1 µg/ml aprotinin, 1 µg/ml leupeptin) and kept at 4° C. and supernatant were collected. Resolved proteins were transferred on to the PVDF membrane. After a quick wash in PBST (Phosphate buffered saline and 0.1% Tween 20), the membranes were blocked in 5% nonfat dry milk in PBS for at least 1 hour and then incubated with primary antibodies (anti-hPaf1/PD2, anti-ALDH1, anti-CD133, anti-CD44, anti-Shh and anti-β-actin) (diluted in 3% BSA in PBS) for overnight at 4° C. Then the membrane was washed (3×10 minutes) in PBST at room temperature and probed with 1:2000 diluted horseradish peroxidase-conjugated anti-mouse or anti-rabbit secondary antibodies for 1 hour at room temperature and washed 5×10 minutes with PBST. The signal was detected with an ECL chemiluminescence kit (Amersham Bioscience, UK).

Confocal Microscopy

Cells were plated onto sterile round cover slips (CIR 18-1 Fisher brand 12-545-10) and grown in 12-well plates for 24 hours. Cells were fixed in acetone/methanol (1:1; pre-chilled to −20° C.) and permeabilized with 0.1% Triton X-100 in PBS. Then the cells were washed in PBS and incubated with primary-hPaf1/PD2 and CD133 (for two hours) and fluorescent tagged secondary antibodies-both FITC and Texas-red tagged (for 30 minutes) at room temperature. Antibodies were diluted in 5% goat serum. Finally, cover slips were mounted with Vectashield® mounting medium containing DAPI (4',6-diamidino-2-phenylindole; VECTOR).

Results

Figure 1B:
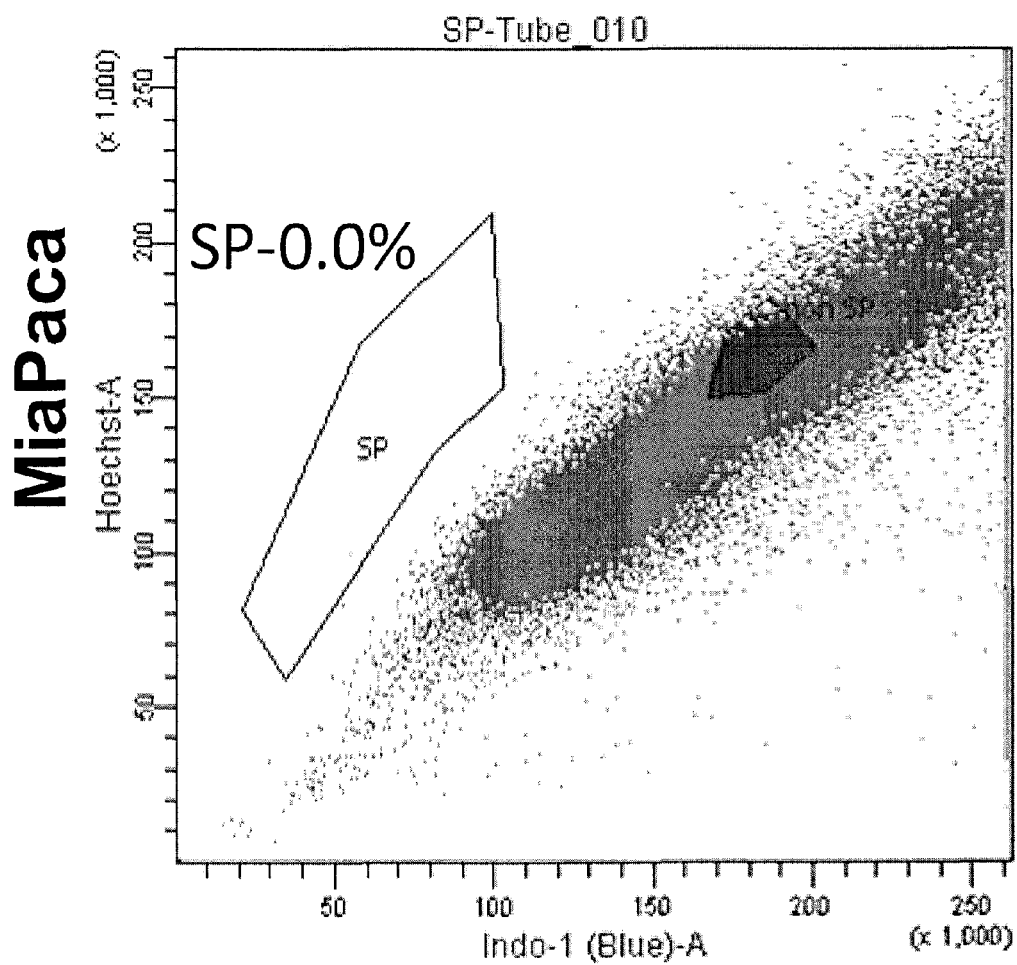
Figure 1C:
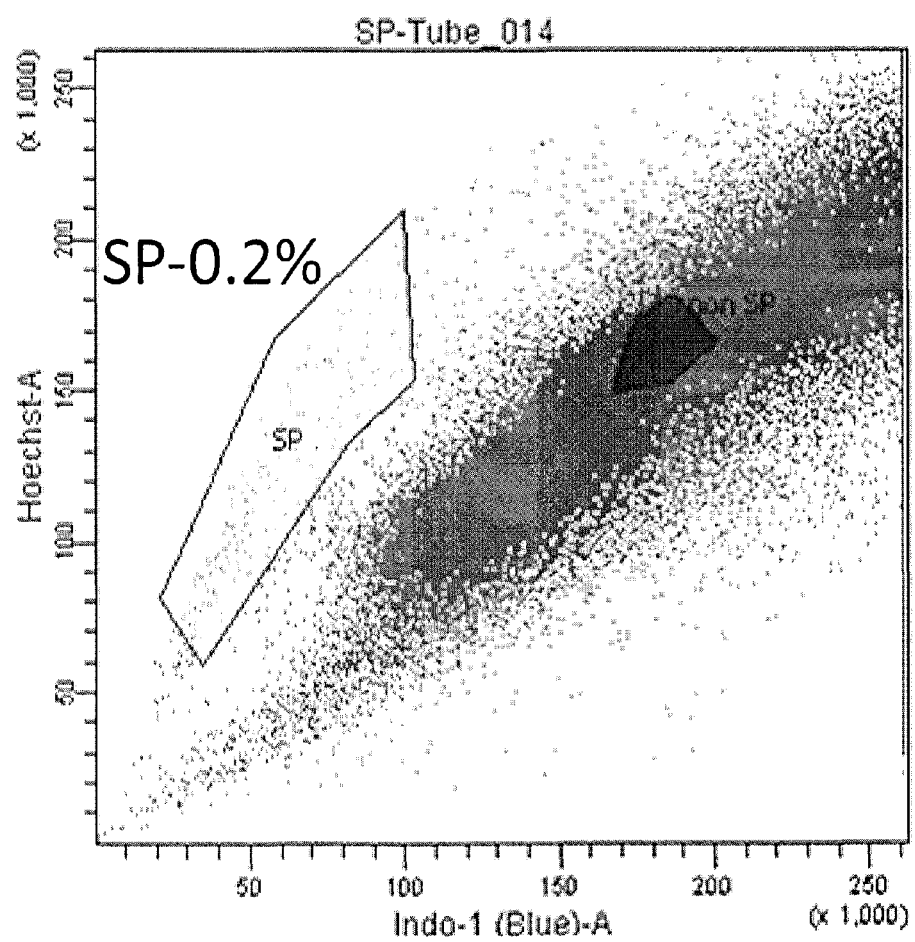
Figure 1D:
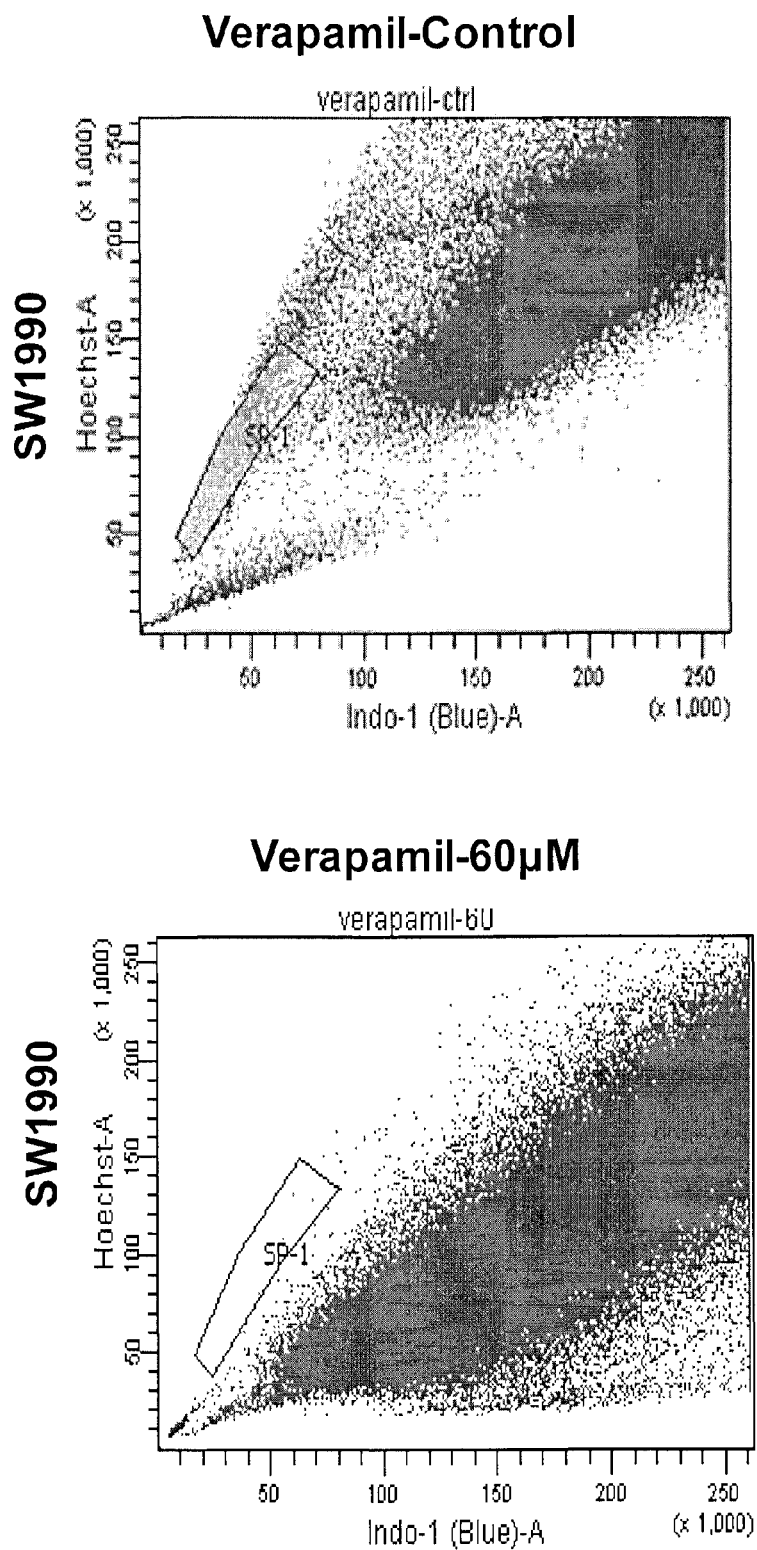
Figure 2A:
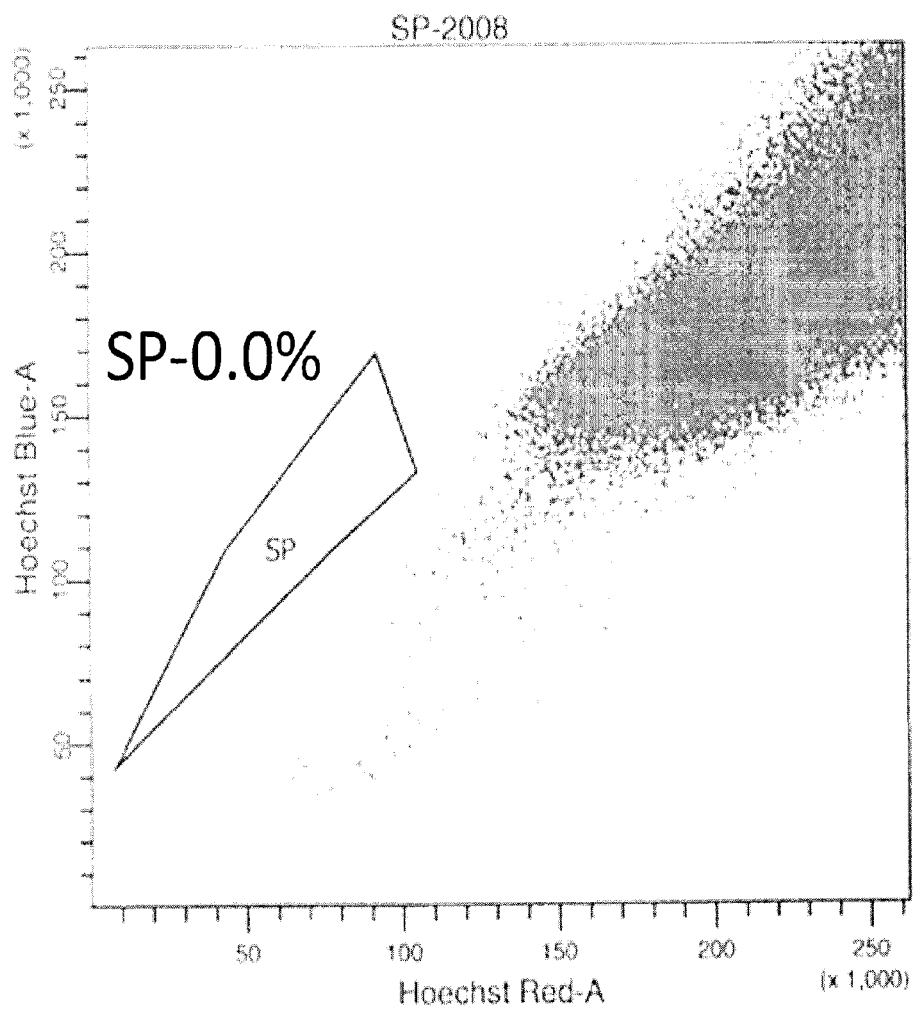
FIG. 2 provides the analysis and characterization of SP and NSP cells in Hoechst 33342 dye in ovarian cancer cells. For FIGS. 2A-2C, the SP cells in ovarian cancer cells (2008—0.0%, A2780—0.0% and OVCAR3—0.5%) were sorted by FACS analysis. OVCAR3—0.6% SP cells were isolated and maintained in stem cell specific condition.
FIG. 2D shows that cobblestone morphology was observed in OVCAR3-SP cells compared to NSP cells.
FIG. 2E provides a tumorsphere assay that showed bigger size and increased number of spheres in SP cells compared to NSP cells.
Figure 2B:
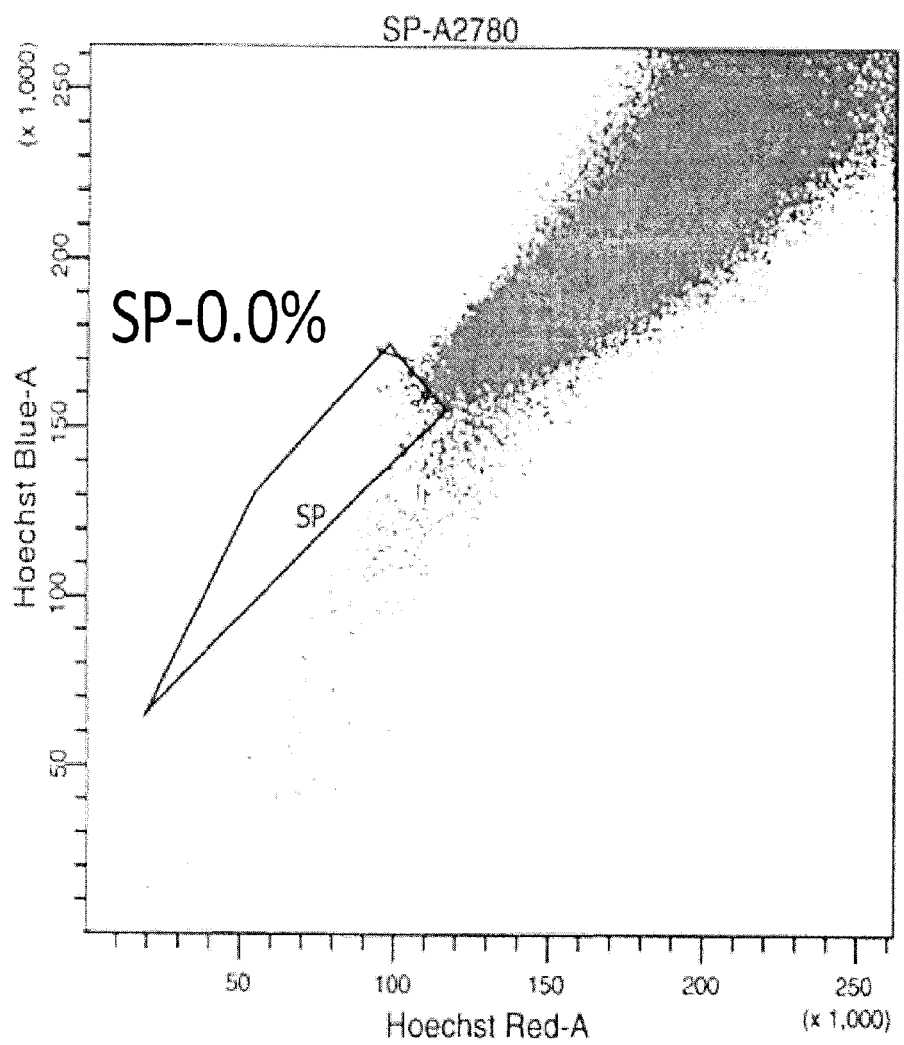
Figure 2C:
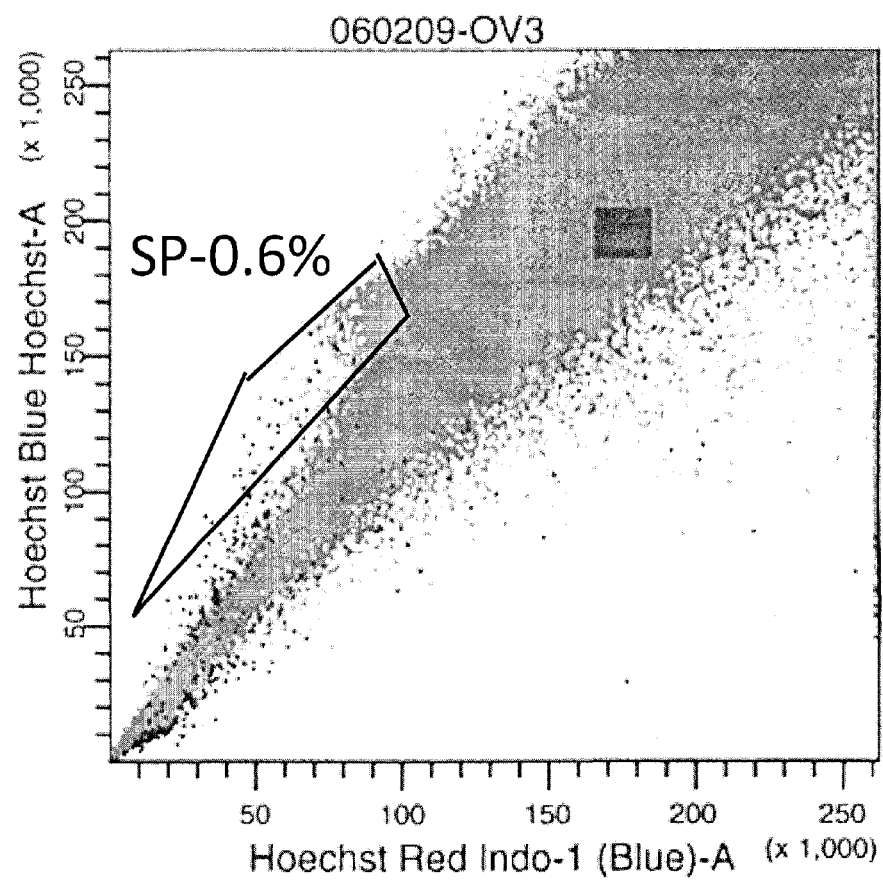
Figure 2D:
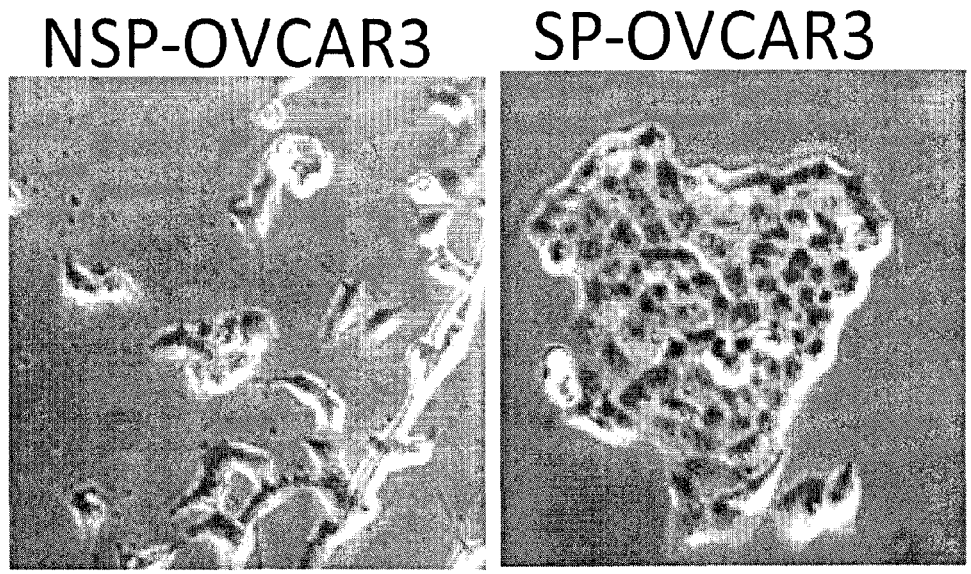

Isolation and Characterization of SP and NSP Cells from Both Pancreatic and Ovarian Cancer Cells Recently, cancer stem cells have been identified as a minor population of cells within the cancer cell population which can be sorted by flow cytometry based on their capacity to efflux the fluorescent DNA-binding dye, Hoechst 33342. This is due to their overexpression of the ABCG2 drug resistance protein, characteristic of cancer stem/progenitor cells (Bunting, K. D. (2002) Stem Cells 20:11-20; Kim et al. (2002) Clin. Cancer Res., 8:22-28). This population of sorted cells was called side population (SP) and the remaining population was named the non-side population (NSP). In the present study, the number of SP and NSP cells in pancreatic (SW1990, BXPC3 and MiaPaCa) (FIGS. 1A-1C) and ovarian (OVCAR3, A2780 and 2008) (FIGS. 2A-2C) cancer cells was analyzed. SW1990 pancreatic cancer cells showed 0.2% of SP cells and OVCAR3 ovarian cancer cells showed 0.6% of SP cells whereas other cells (MiaPaCa, BXPC3, A2780 and 2008) showed minimal or no SP population. SP and NSP cells were isolated from both SW1990 (PC) and OVCAR3 (OC) cells by Hoechst 33342 by FACS sorting method. In parallel, verapamil (a calcium channel inhibitor that reverses the multidrug resistance) was used to ensure that the isolated cells were purely SP cells (FIG. 1D).

Figure 2E:
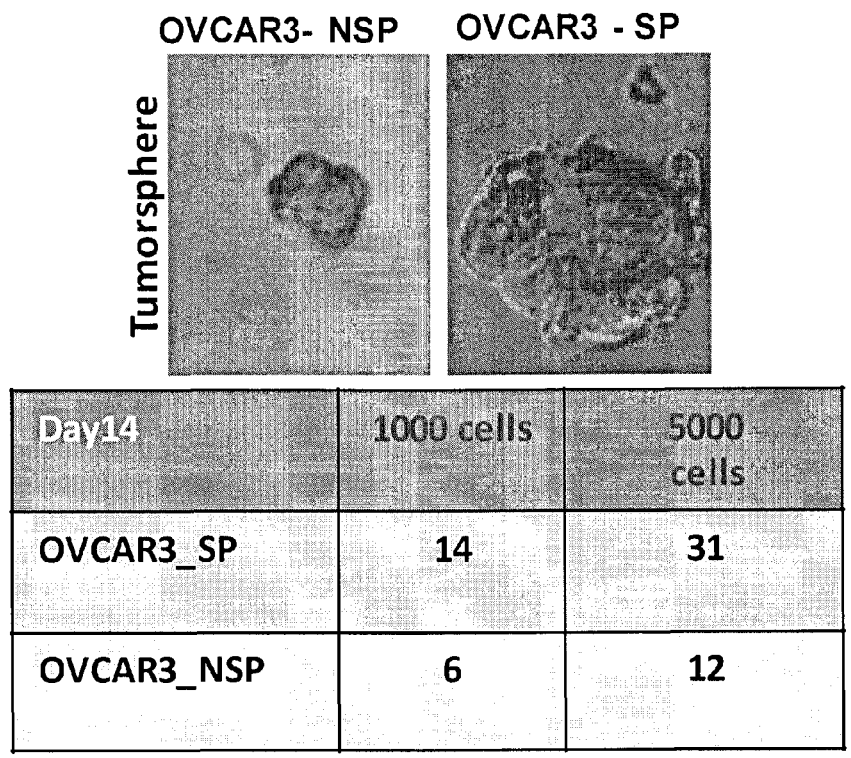
Figure 3A:
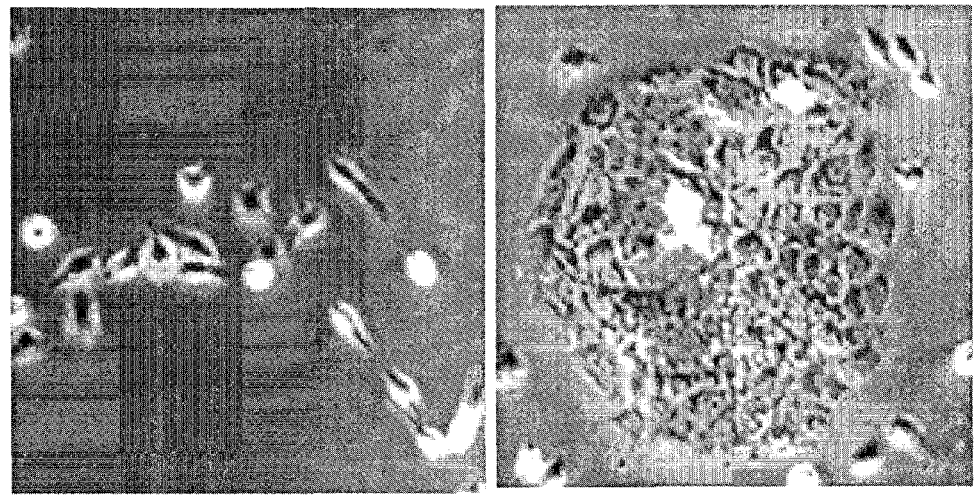
FIG. 3 demonstrates the in vitro and in vivo characterization of isolated SP and NSP cells. For FIG. 3A, SP and NSP cells were grown in culture under stem cell specific condition. SP cells morphology showed circular colony formation (cobblestone appearance) compared to NSP cells in both SW1990 and OVCAR3 cells. For FIGS. 3B and 3C, SP and NSP cells were seeded at a low density 1000-5000 cells/well in six-well ultra-low attachment plate with stem cell specific media. Tumor spheres assay showed both increased number and size of sphere formation in SP cells compared to NSP cells. For FIG. 3D, isolated SP and NSP cells were injected subcutaneously in dorsal fat pad of nude mice (right side SP cells and left side NSP cells). The tumor growth was observed after 4 weeks and animals were killed after 7 weeks. SP cells showed significant size of tumor growth and no tumor was found in NSP cells.
Figure 3B:
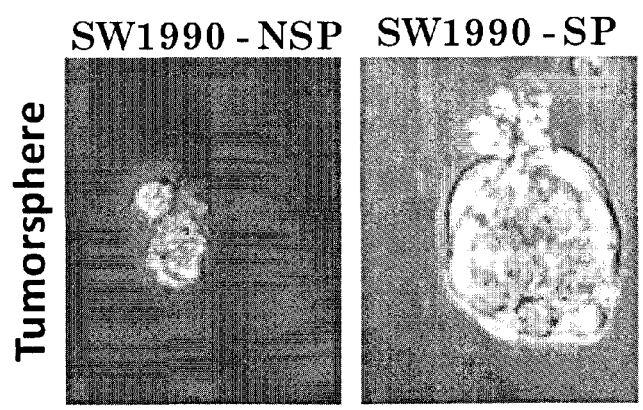

Isolated SP and NSP cells from both SW1990 and OVCAR3 were grown in vitro under stem cell specific condition (details are mentioned in materials and methods section). SP cells showed tight junctions and circular colony formation in both SW1990 and OVCAR3 cells (FIG. 3A), whereas NSP cells grew like differentiated cell type. Formation of spherical colonies has been reported to be a property of stem/progenitor cells and verifies a high developmental and proliferative potential of SP cells (Engelmann et al. (2008) Cancer Res., 68:2419-2426). Interestingly, increased number of larger tumorspheres in SP cells were observed compared to NSP cells in both pancreatic cancer (FIG. 3B) and ovarian (FIG. 2E) cancer model. This confirms that the isolated SP cells behave like cancer stem cell population.

Figure 3C:
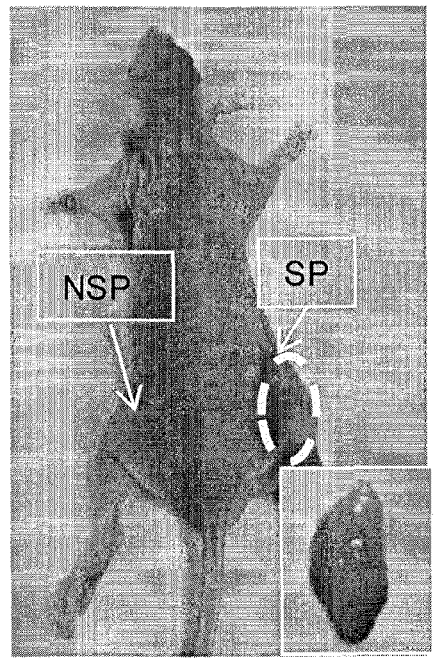
Figure 3D:
Figure 3D:
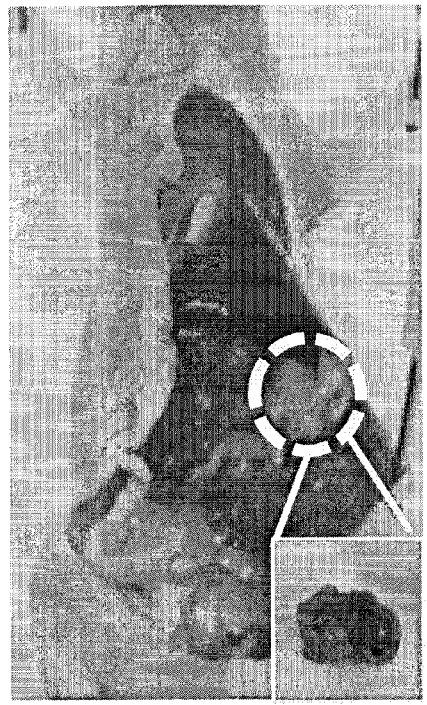

Promoting tumorigenesis is one of the important properties of cancer stem cell population. To explore the potential tumorigenic character of isolated SP cells, low number (~5000 cells) of SP and NSP cells isolated from SW1990 cells were subcutaneously injected with matrigel in athymic mice. The animals were monitored at regular intervals and tumor growth was observed after 4 weeks only in the SP cells injected side (FIG. 3C). The mice were sacrificed after 7 weeks and significant tumor growth was observed in SP cells whereas NSP cells did not form tumors (FIG. 3C). Furthermore, pancreatic orthotopic implantation of both SP and NSP cells, isolated from SW1990 cells, was performed in athymic nude mice. After 6 weeks, the animals were sacrificed and tumor formation was observed with an average weight of 325 mg only in SP cells injected mice while no tumor developed in NSP cells injected mice (FIG. 3D). This result indicates that the isolated SP cells were highly tumorigenic in nature and were used for further analysis.

Figure 4A:
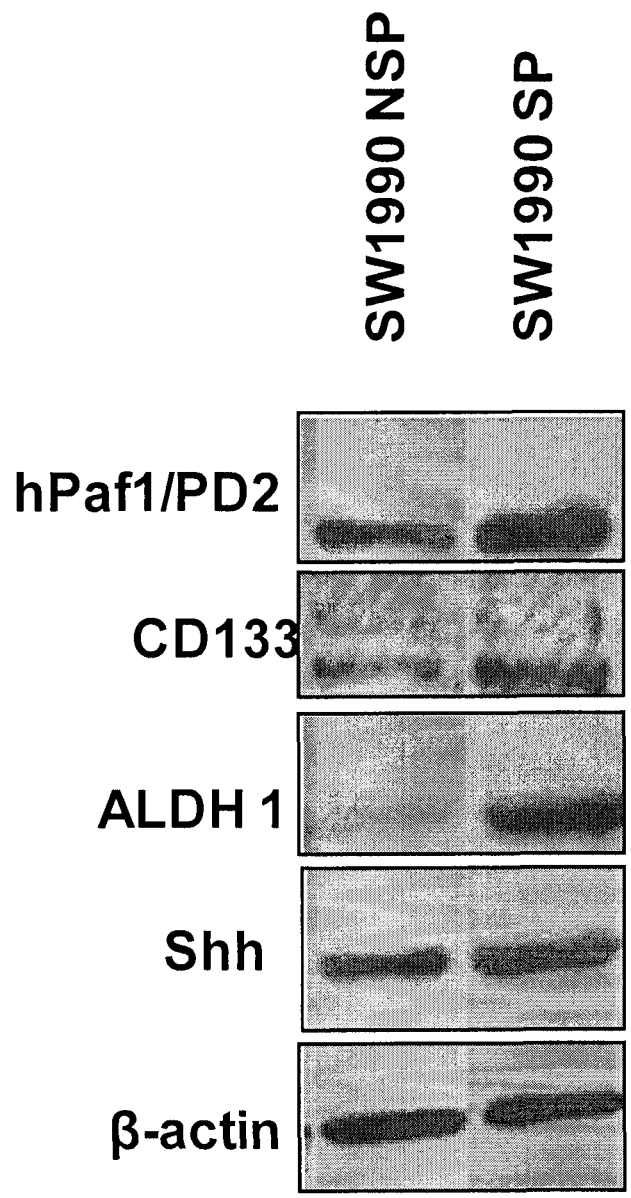
FIG. 4A provides a Western blot analysis showed increased expression of PD2 in isolated SP cells along with cancer stem cell specific markers (CD133 and ALDH1) and also the self-renewal marker SHH in SW1990-SP cells compared to NSP cells. β-actin was used as a loading control.
Figure 4B:
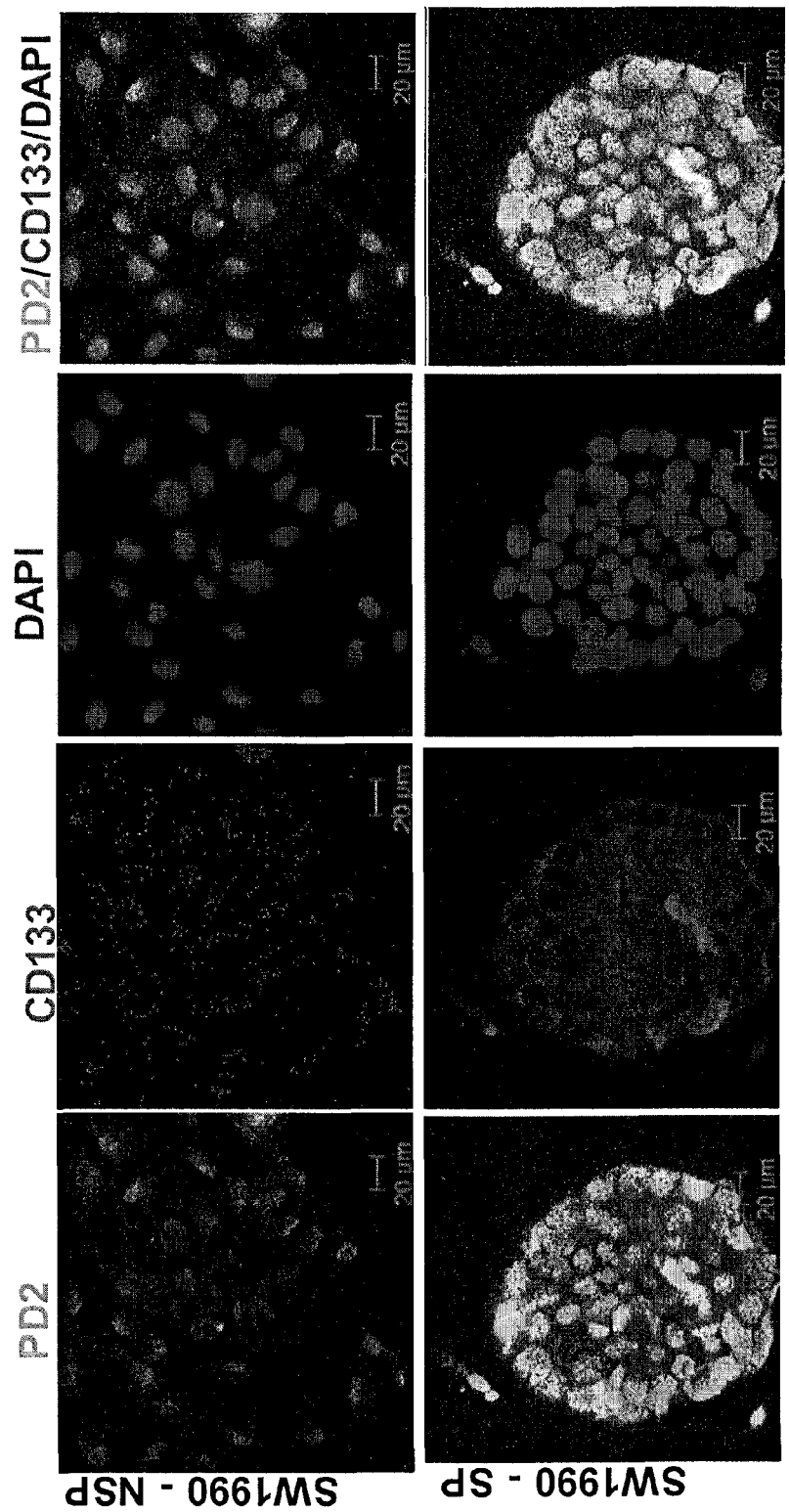
FIGS. 4B and 4C provide a confocal analysis showed increased expression of hPaf1/PD2 along with CSC markers (CD133 and ALDH1) in SP cells compared to NSP cells (DAPI-Nuclear staining).
Figure 4C:
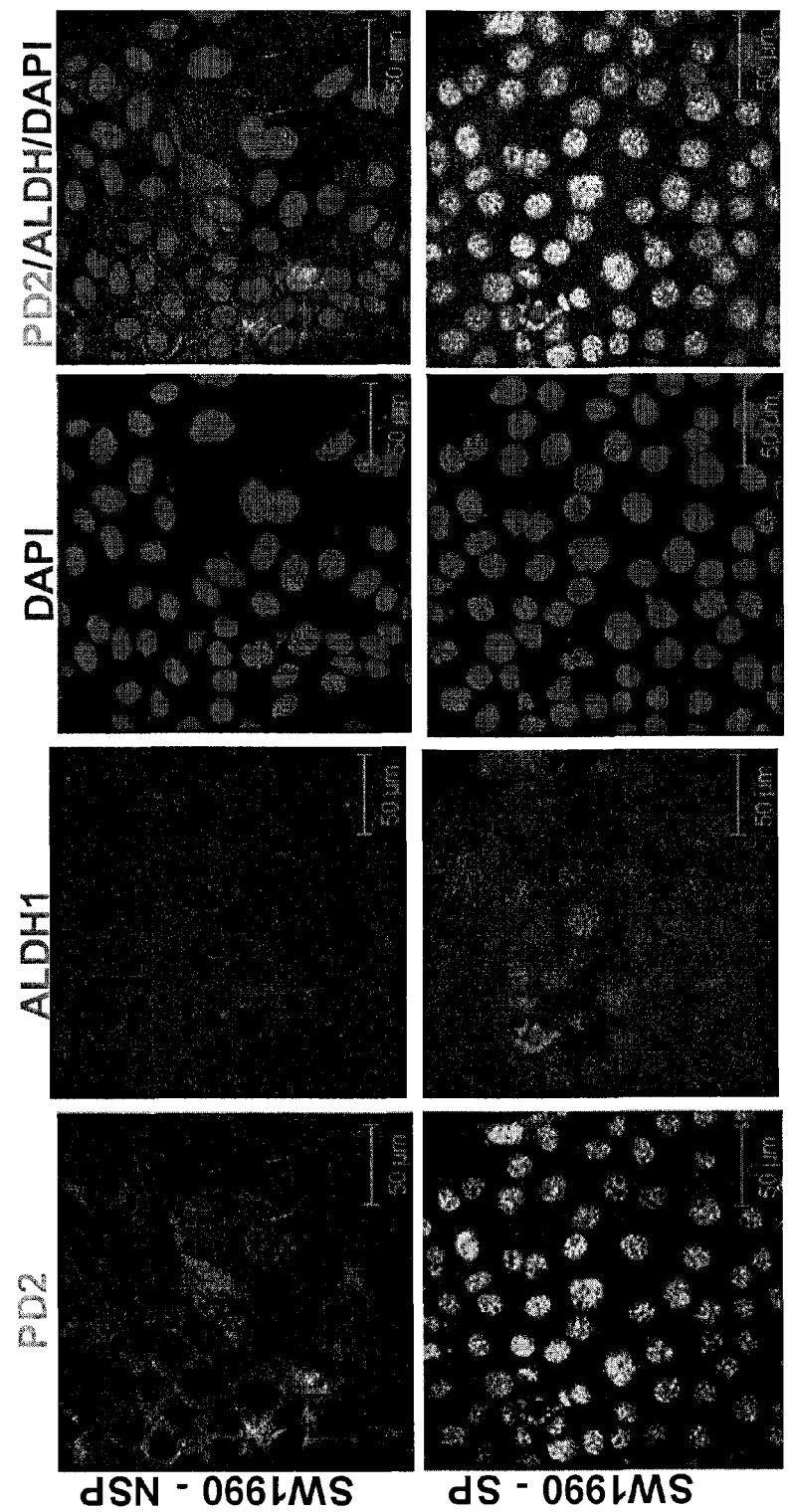
Figure 5A:
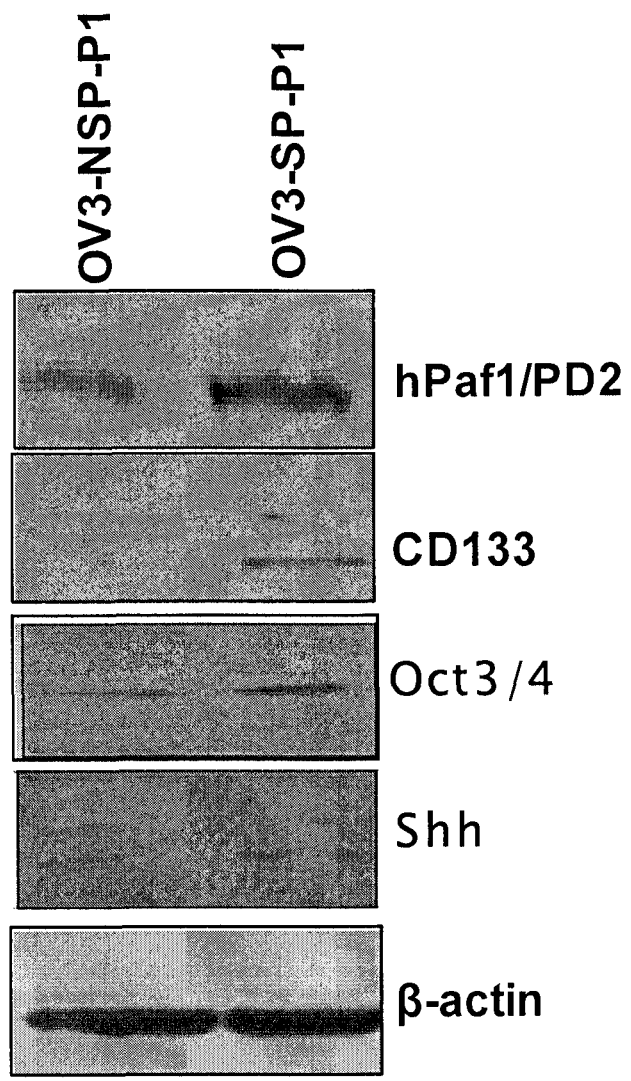
FIG. 5 shows the expression of hPaf1/PD2 in both SP and NSP cells from OVCAR3 cells. Western blot analysis showed the increased expression of hPaf1/PD2 along with cancer stem cell specific marker CD133 and self-renewal marker Oct/4 and Shh. SP and NSP cells were plated onto sterile round cover slips and grown in 12-well plates for 24 hours followed by confocal immunofluorescence procedure. Confocal analysis showed increased expression of hPaf1/PD2 and CD133 in SP cells compared to NSP cells. DAPI was used as a nuclear staining.
Figure 5B:
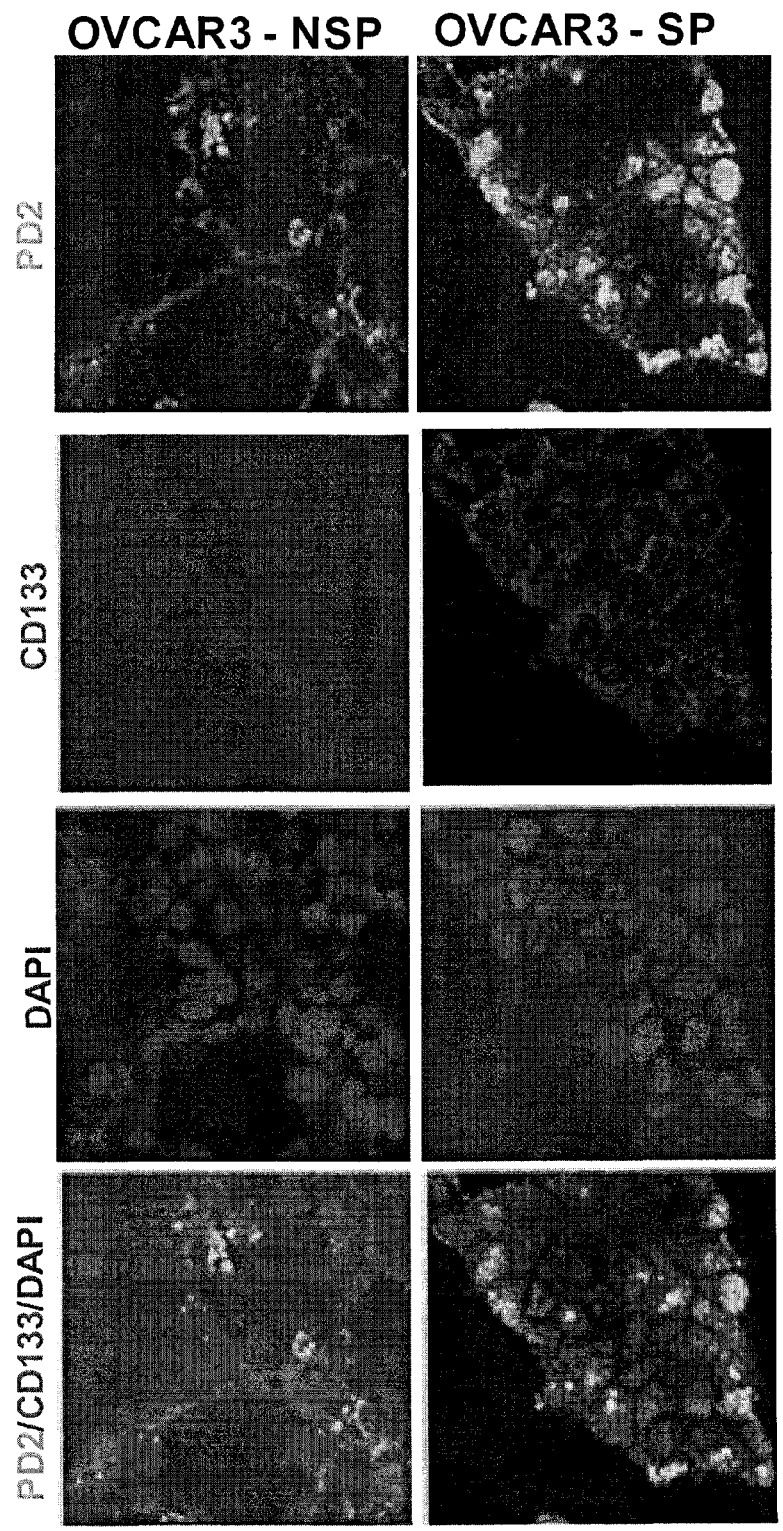
Figure 6A:
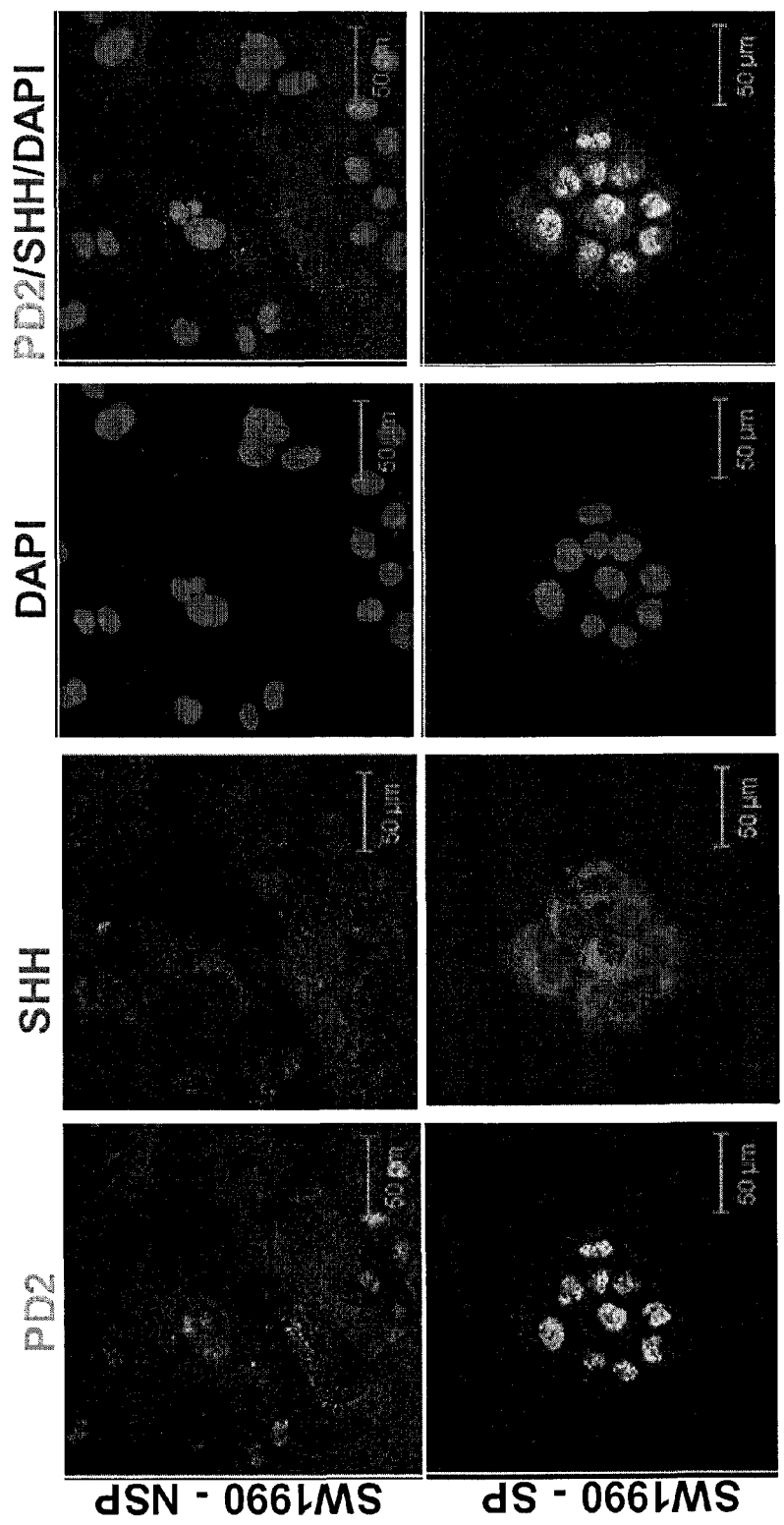
FIGS. 6A-6C show self-renewal markers in isolated SP cells. Confocal analysis showed set (SHH, Oct3/4 and beta-catenin) of self-renewal marker expression in SW1990-SP cells. First panel showed the increased expression of Shh along with hPaf1/PD2 in SP cells compared to NSP cells. The second panel showed the increased expression of Oct3/4 along with hPaf1/PD2 in SP cells compared to NSP cells. Third panel showed the membrane localization and increased expression of beta-catenin along with hPaf1/PD2 expression. DAPI was used for nuclear staining.
Figure 6B:
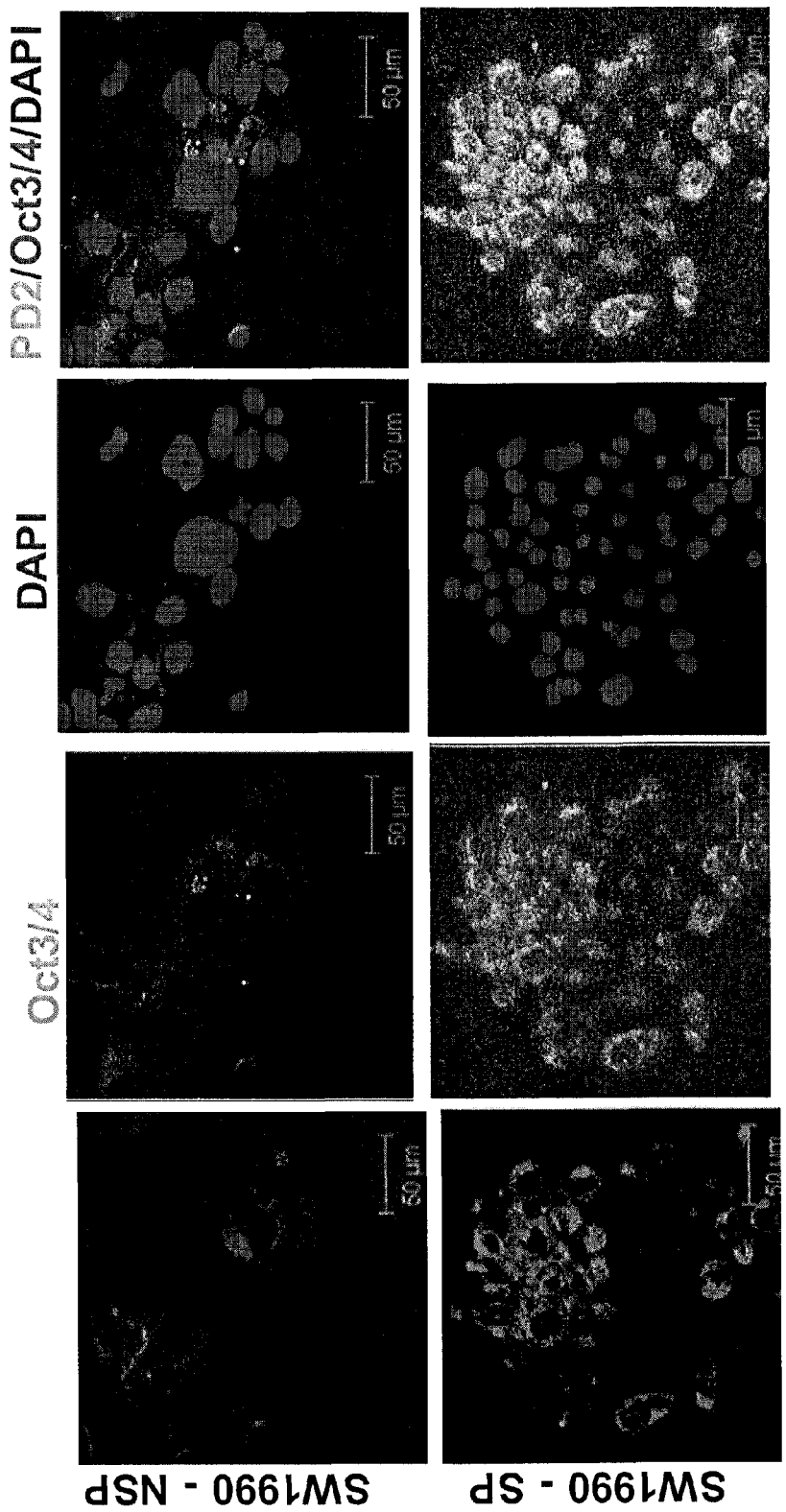
Figure 6C:
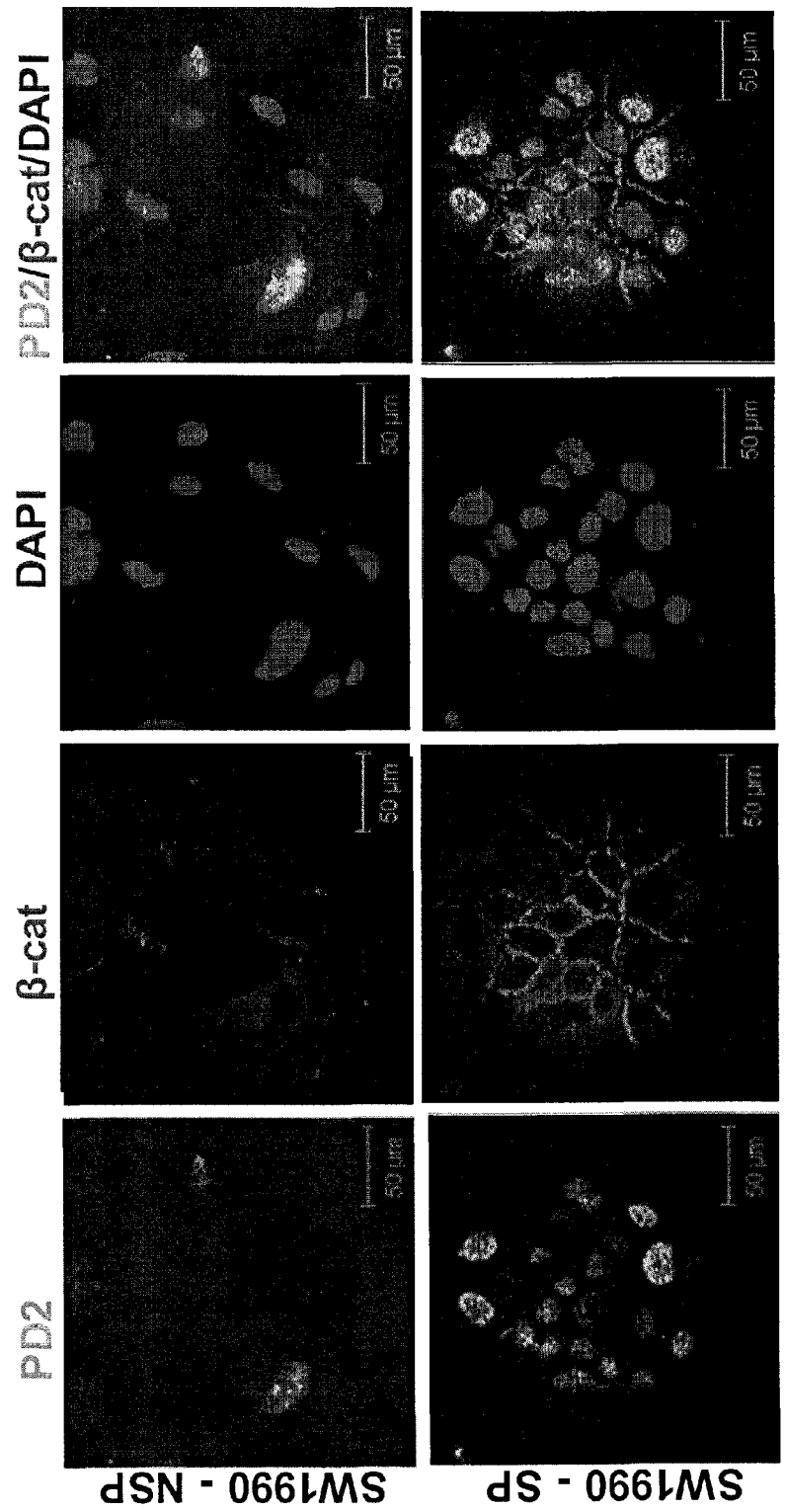

Preferential Expression of hPaf1/PD2 and Cancer Stem Cell Specific Markers in SP Cells Cancer stem cells have been demonstrated to express several universal stem cell markers such as CD133, CD44, CD24, ESA and ALDH1 in different cancers (Ponnusamy et al. (2008) J. Ovarian Res., 1:4). Stem cells and cancer stem cells are known to possess the phenomenal property of self-renewal which is maintained by few specific pathways such as Shh, Wnt and Notch (Ponnusamy et al. (2008) J. Ovarian Res., 1:4). These markers were used for the confirmation of the isolated cancer stem cell population. It has been shown that Paf1/PD2 is aberrantly expressed in mouse embryonic stem cells and maintains self-renewal process by the interaction with Oct3/4 (Ponnusamy et al. (2009) Stem Cells 27:3001-3011). In this study, hPaf1/PD2 was analyzed along with CD133, ALDH1, Oct3/4 and Shh cancer stem cell markers in both SP and NSP cells from SW1990 and OVCAR3 cells. Interestingly, hPaf1/PD2 showed significantly elevated expression along with CD133, ALDH1 and Shh in SW1990-SP cells compared to NSP cells (FIG. 4A). The expression levels of hPaf1/PD2 and ALDH1 were stable up to the third cell passage when maintained under stem cell specific condition. This indicates that when maintained under stem cell specific condition, the isolated cancer stem cell population were enriched even in third passage. Similarly, the hPaf1/PD2 was also found to be overexpressed in OVCAR3-SP cells along with CD133, Oct3/4 and Shh (FIG. 5A). hPaf1/PD2 expression along with CD133 was also confirmed by confocal immunofluorescence analysis (FIG. 5A). These results indicate that the isolated SP cells show significant hPaf1/PD2 expression in both pancreatic and ovarian cancer cells. Self-renewal markers Oct3/4, Shh and β-catenin showed significantly elevated expression in SW1990-SP cells compared to NSP cells (FIGS. 6A-6C) by confocal immunofluorescence analysis.

Drug Treatment Enriches the Cancer Stem Cell Population

Figure 7A:
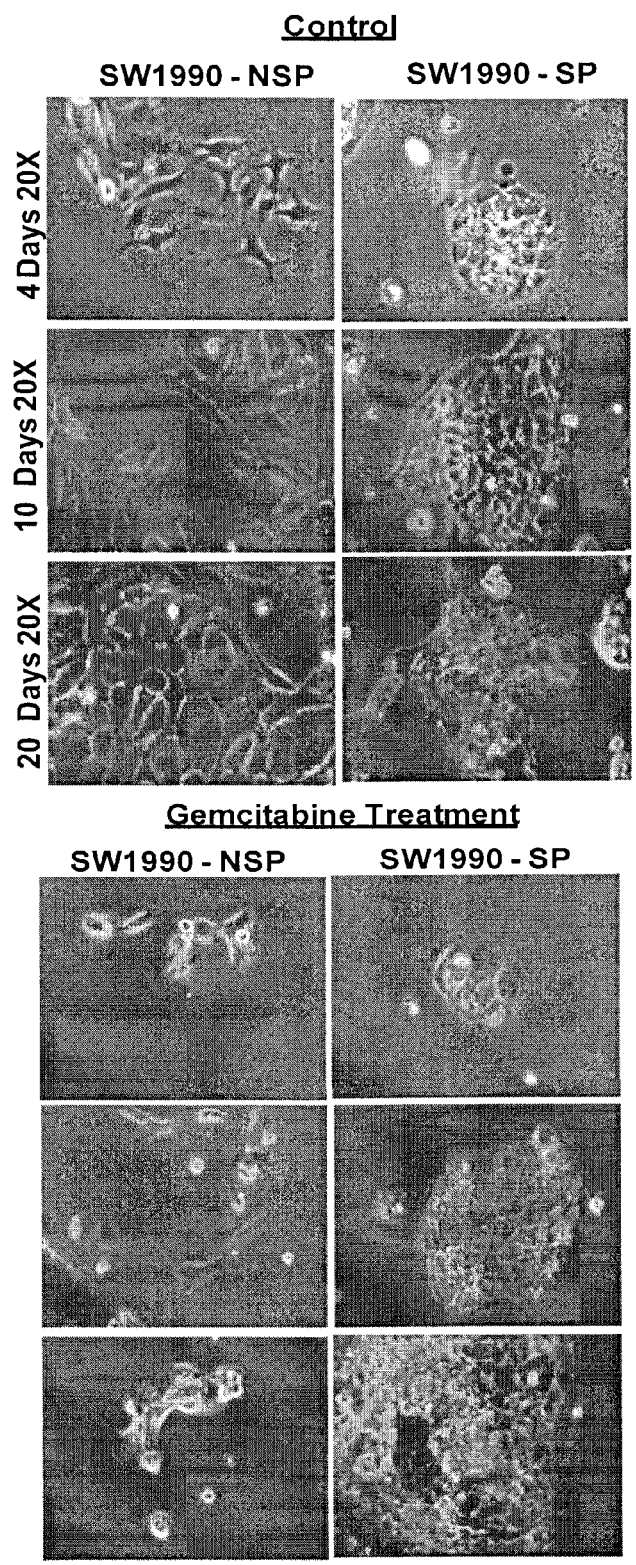
FIG. 7 provides the drug sensitivity of cancer stem cells (SP) and non-cancer stem cells (NSP) on different days of treatment. Gemcitabine (6 μM) treatment was used for 20 days in both SW1990-SP and NSP cells. SP cells grew well with characteristic phenotype upon gemcitabine treatment compared to NSP cells (FIG. 7A).
FIG. 7B provides a Western blot analysis showed expression of hPaf1/PD2 and ALDH1 is maintained in gemcitabine treated SP cells compared to untreated SP cells. β-actin was used as a loading control.
Figure 7B:
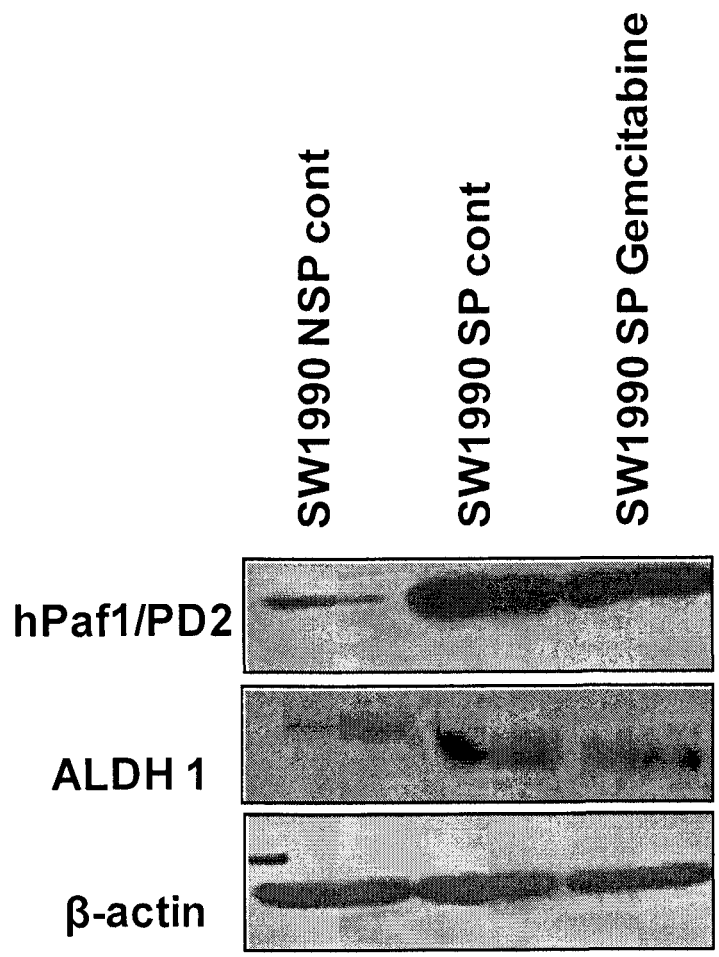

Tumor relapse occurs in cancer patients due to the important phenomena known as drug resistance. It has already been established that drug resistance of cancer stem cells is due to the expression of ABC transporter glycoproteins which are capable of effluxing the drug out of the cell. To investigate their drug resistance efficiency, SW1990 SP and NSP cells have been treated with 6.0 µM concentration of gemcitabine for several days. Cell death was observed on drug treatment in NSP cells whereas SP cells maintained their circular colonies and continued to grow even after 4, 10 and 20 days of treatment (FIG. 7). This indicates that isolated SP cells retain their drug resistance property. The expression of ALDH1 was analyzed in the gemcitabine treated SW1990-SP cells. Interestingly, western blot analysis showed significantly elevated expression of ALDH1 in gemcitabine (6 µM) treated SP cells compared to non-treated SP cells (FIG. 7) indicating progressive enrichment of CSCs upon drug treatment.

Knockdown of hPaf1/PD2 Affects the CSC Phenotype

Figure 8A:
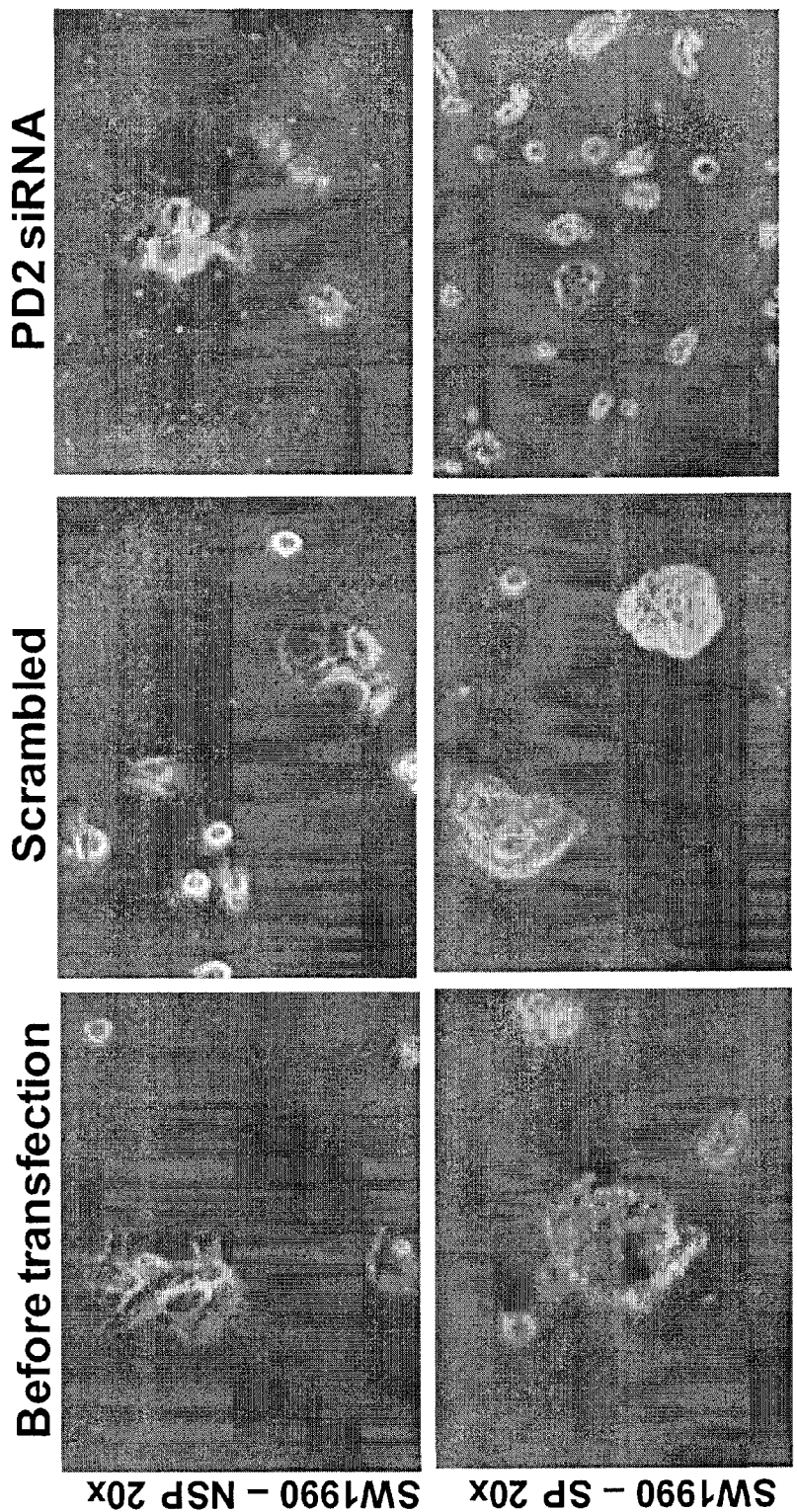
FIG. 8A shows seven days of gemcitabine treatment with the transient knockdown (72 hours) of hPaf1/PD2 in SW1990-SP cells. Knockdown of hPaf1/PD2 and gemcitabine treatment in cancer stem cells (SP) decreased the viability of SP cells and changed its phenotype.
Figure 8B:
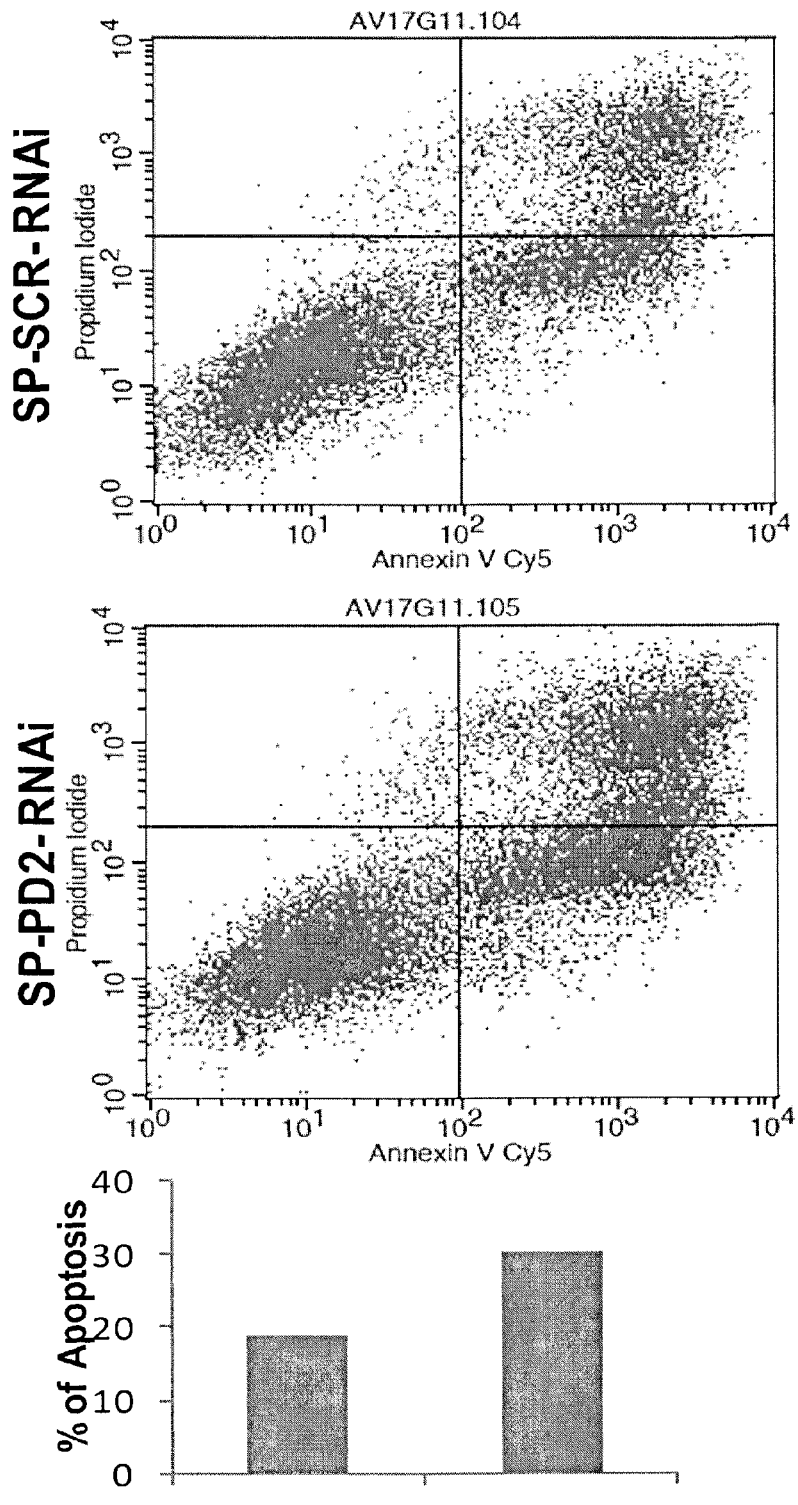
FIG. 8B provides a FACS-apoptosis analysis with PI staining showed increased percentage of cell death in hPaf1/PD2 knockdown SP cells along with gemcitabine treatment compared to control cells.
Figure 8C:
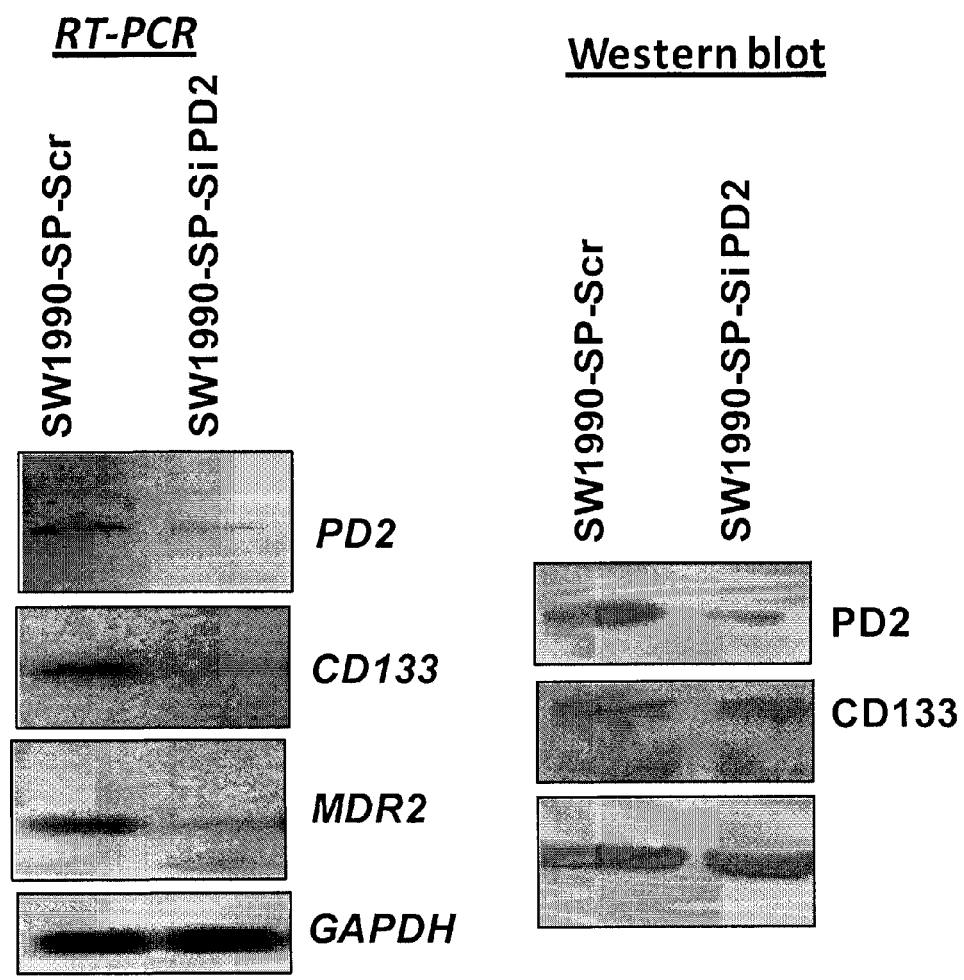
FIG. 8C provides RT-PCR results showing knockdown of hPaf1/PD2 decreases the levels of CD133 and Multi Drug Resistance 2 (MDR2) gene. Western blot result showed decrease expression of CD133 protein in hPaf1/PD2 knockdown cells. GAPDH and β-actin were served as expression control.

Following the previous drug sensitivity experiment, hPaf1/PD2 was transiently knocked down using RNAi oligos. The knockdown was carried out in vitro under stem cell specific culture condition. Interestingly, the results showed that hPaf1/PD2 knockdown SP cells treated with gemcitabine lost their CSC phenotype (FIG. 8A). Further, depletion of hPaf1/PD2 in SP cells promotes apoptosis on gemcitabine treatment (FIGS. 8A and 8B). In addition, RNA was extracted from hPaf1/PD2 knockdown SP cells and control cells for analysis of CSC and drug resistant markers. hPaf1/PD2 knockdown SP cells showed 80% knockdown of PD2 along with decreased CD133 expression at both RNA and protein levels (FIG. 8C). Interestingly, MDR2 (Multi Drug Resistant gene 2) gene also showed decreased expression in hPaf1/PD2 knockdown SP cells on gemcitabine treatment compared to control cells (FIG. 8C). These results indicate that hPaf1/PD2 is involved in the maintenance of cancer stem cell population by controlling the drug resistance and self-renewal process.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a drug resistant cancer in a subject in need thereof, said method comprising:
    a) administering at least one human polymerase associated factor/pancreatic differentiation 2 (hPaf1/PD2) antagonist to said subject, and
    b) administering at least one chemotherapeutic agent to said subject.

2. The method of claim 1, wherein said hPaf1/PD2 antagonist is an inhibitory nucleic acid molecule.

3. The method of claim 2, wherein said inhibitory nucleic acid molecule is selected from the group consisting of antisense molecule, siRNA, and shRNA.

4. The method of claim 2, wherein said inhibitory nucleic acid molecule comprises a sequence which is complementary to a nucleic acid molecule encoding SEQ ID NO: 2.

5. The method of claim 3, wherein said siRNA comprises SEQ ID NO: 1 or SEQ ID NO: 5.

6. The method of claim 1, wherein said cancer is pancreatic or ovarian cancer.

7. The method of claim 1, wherein said hPaf1/PD2 antagonist is administered to said subject at least prior to the administration of said chemotherapeutic agent.

8. The method of claim 1, wherein said cancer is resistant to the chemotherapeutic agent administered in step b).

9. The method of claim 1, wherein said chemotherapeutic agent is a pyrimidine analog.

10. The method of claim 9, wherein said chemotherapeutic agent is gemcitabine.

11. The method of claim 1, wherein said chemotherapeutic agent is selected from the group consisting of cisplatin, gemcitabine, doxorubicin, 5-fluoruracil, cyclophosphamide, dactinomycin, levamisole, etoposide, topotecan, thiotepa, vinblastine, paclitaxel, and docetaxel.

12. The method of claim 1,
    wherein said hPaf1/PD2 antagonist is an inhibitory nucleic acid molecule, and
    wherein said cancer is pancreatic or ovarian cancer.

13. The method of claim 12, wherein said cancer is resistant to the chemotherapeutic agent administered in step b).

14. The method of claim 13, wherein said chemotherapeutic agent is gemcitabine.

* * * * *

SEQUENCE LISTING

<160> NUMBER OF SEQ ID NOS: 5

<210> SEQ ID NO 1
<211> LENGTH: 21
<212> TYPE: RNA
<213> ORGANISM: Artificial Sequence
<220> FEATURE:
<223> OTHER INFORMATION: siRNA strand

<400> SEQUENCE: 1
aacagguucg uccaguacaa a        21

<210> SEQ ID NO 2
<211> LENGTH: 531

<212> TYPE: PRT
<213> ORGANISM: Homo sapiens

<400> SEQUENCE: 2

```
Met Ala Pro Thr Ile Gln Thr Gln Ala Gln Arg Glu Asp Gly His Arg
 1               5                  10                  15

Pro Asn Ser His Arg Thr Leu Pro Glu Arg Ser Gly Val Val Cys Arg
            20                  25                  30

Val Lys Tyr Cys Asn Ser Leu Pro Asp Ile Pro Phe Asp Pro Lys Phe
        35                  40                  45

Ile Thr Tyr Pro Phe Asp Gln Asn Arg Phe Val Gln Tyr Lys Ala Thr
    50                  55                  60

Ser Leu Glu Lys Gln His Lys His Asp Leu Leu Thr Glu Pro Asp Leu
65                  70                  75                  80

Gly Val Thr Ile Asp Leu Ile Asn Pro Asp Thr Tyr Arg Ile Asp Pro
                85                  90                  95

Asn Val Leu Leu Asp Pro Ala Asp Glu Lys Leu Leu Glu Glu Glu Ile
            100                 105                 110

Gln Ala Pro Thr Ser Ser Lys Arg Ser Gln Gln His Ala Lys Val Val
        115                 120                 125

Pro Trp Met Arg Lys Thr Glu Tyr Ile Ser Thr Glu Phe Asn Arg Tyr
    130                 135                 140

Gly Ile Ser Asn Glu Lys Pro Glu Val Lys Ile Gly Val Ser Val Lys
145                 150                 155                 160

Gln Gln Phe Thr Glu Glu Ile Tyr Lys Asp Arg Asp Ser Gln Ile
                165                 170                 175

Thr Ala Ile Glu Lys Thr Phe Glu Asp Ala Gln Lys Ser Ile Ser Gln
            180                 185                 190

His Tyr Ser Lys Pro Arg Val Thr Pro Val Glu Val Met Pro Val Phe
        195                 200                 205

Pro Asp Phe Lys Met Trp Ile Asn Pro Cys Ala Gln Val Ile Phe Asp
    210                 215                 220

Ser Asp Pro Ala Pro Lys Asp Thr Ser Gly Ala Ala Ala Leu Glu Met
225                 230                 235                 240

Met Ser Gln Ala Met Ile Arg Gly Met Met Asp Glu Gly Asn Gln
                245                 250                 255

Phe Val Ala Tyr Phe Leu Pro Val Glu Glu Thr Leu Lys Lys Arg Lys
            260                 265                 270

Arg Asp Gln Glu Glu Glu Met Asp Tyr Ala Pro Asp Asp Val Tyr Asp
        275                 280                 285

Tyr Lys Ile Ala Arg Glu Tyr Asn Trp Asn Val Lys Asn Lys Ala Ser
    290                 295                 300

Lys Gly Tyr Glu Glu Asn Tyr Phe Phe Ile Phe Arg Glu Gly Asp Gly
305                 310                 315                 320

Val Tyr Tyr Asn Glu Leu Glu Thr Arg Val Arg Leu Ser Lys Arg Arg
                325                 330                 335

Ala Lys Ala Gly Val Gln Ser Gly Thr Asn Ala Leu Leu Val Val Lys
            340                 345                 350

His Arg Asp Met Asn Glu Lys Glu Leu Glu Ala Gln Glu Ala Arg Lys
        355                 360                 365

Ala Gln Leu Glu Asn His Glu Pro Glu Glu Glu Glu Glu Met
    370                 375                 380

Glu Thr Glu Glu Lys Glu Ala Gly Gly Ser Asp Glu Glu Gln Glu Lys
385                 390                 395                 400
```

Gly Ser Ser Ser Glu Lys Glu Gly Ser Glu Asp His Ser Gly Ser
            405                 410                 415

Glu Ser Glu Arg Glu Glu Gly Asp Arg Asp Glu Ala Ser Asp Lys Ser
        420                 425                 430

Gly Ser Gly Glu Asp Glu Ser Glu Asp Glu Ala Arg Ala Ala Arg
        435                 440                 445

Asp Lys Glu Glu Ile Phe Gly Ser Asp Ala Asp Ser Glu Asp Ala
    450                 455                 460

Asp Ser Asp Asp Glu Asp Arg Gly Gln Ala Gln Gly Ser Asp Asn
465                 470                 475                 480

Asp Ser Asp Ser Gly Ser Asn Gly Gly Gly Arg Ser Arg Ser His
            485                 490                 495

Ser Arg Ser Ala Ser Pro Phe Pro Ser Gly Ser Glu His Ser Ala Gln
        500                 505                 510

Glu Asp Gly Ser Glu Ala Ala Ala Ser Asp Ser Glu Ala Asp Ser
        515                 520                 525

Asp Ser Asp
    530

<210> SEQ ID NO 3
<211> LENGTH: 1937
<212> TYPE: DNA
<213> ORGANISM: Homo sapiens

<400> SEQUENCE: 3

```
ttctcgcccg cccacctcat ctcaacccac tttccgcggg gagcggcgcc aagctgggcc      60
ttcctcggat caggcgtccc ctgaagtcgg cacgcccctc tgcgtccccc ttcggtcccg     120
ctaggacccc gtccgggctg ccgtcgcctc gtcgctatgg cgccaccat ccagacccag      180 gcccagcggg aggatggcca caggcccaat cccaccggga ctctgcctga gaggtctgga     240
gtggtctgcc gagtcaagta ctgcaatagc ctccctgata tccccttcga ccccaagttc     300
atcacctacc ccttcgacca gaacaggttc gtccagtaca agccacttc cttggagaaa     360 cagcacaaac atgacctcct gactgagcca gactgggggg tcaccatcga tctcatcaat     420
cctgacacct accgcatcga ccccaatgtt cttctagatc cagctgatga gaaacttttg     480
gaagaggaga ttcaggcccc caccagctcc aagagatccc agcagcacgc gaaggtggtg     540
ccatggatgc gaaagacaga gtacatctcc actgagttca accgttatgg catctccaat     600
gagaagcctg aggtcaagat tgggggttct gtgaagcagc agtttaccga ggaagaaata     660
tacaaagaca gggatagcca gatcacagcc attgagaaga cttttgagga tgcccagaaa     720
tcaatctcac agcattacag caaaccccga gtcacaccgg tggaggtcat gcctgtcttc     780
ccagacttta agatgtggat caatccatgt gctcaggtga tctttgactc agacccagcc     840
cccaaggaca cgagtggtgc agctgcgttg gagatgatgt ctcaggccat gattaggggc     900
atgatggatg aggaagggaa ccagtttgtg gcctatttcc tgcctgtaga agagacgttg     960
aagaaacgaa agcgggacca ggaggaggag atggactatg caccagatga tgtgtatgac    1020
tacaaaattg ctcgggagta caactggaac gtgaagaaca agctagcaa gggctatgag    1080 gaaaactact tcttcatctt ccgagagggt gacggggttt actacaatga gttggaaacc    1140
agggtccgcc ttagtaagcg ccgggccaag gctggggttc agtcaggcac caacgccctg    1200
cttgtggtca acatcggga catgaatgag aaggaactgg aagctcagga ggcacggaag    1260
gcccagctag aaaaccacga accggaggag gaagaggaag aggagatgga gacagaagag    1320
```

```
aaagaagctg ggggctcaga tgaggagcag gagaagggca gcagcagtga aaggagggc      1380 agtgaagatg agcactcggg cagcgagagt gaacgggagg aaggtgacag ggacgaggcc     1440
agtgacaaga gtggcagtgg tgaggacgag agcagcgagg atgaggcccg ggctgcccgt     1500
gacaaagagg agatctttgg cagtgatgct gattctgagg acgatgccga ctctgatgat     1560
gaggacagag gacaggccca aggtggcagt gacaatgatt cagacagcgg cagcaatggg     1620
ggtggccagc ggagccggag ccacagccgc agcgccagtc ccttccccag tggcagcgag     1680
cactcggccc aggaggatgg cagtgaagct gcagcttctg attccagtga agctgatagt     1740
gacagtgact gagtcccagg gcattcaggg ctggttcaga caccattatt gtgagcagca     1800
aagcactttt ctagtggtct gtttgtgagc ctttcacttg tttgttcccc accccaaac     1860 ctttgctgtt aataaagtca acttctcttt aaaaaaaaaa aaaaaaaaaa aaaaaaaaa     1920 aaaaaaaaaa aaaaaaa                                                   1937

<210> SEQ ID NO 4
<211> LENGTH: 1596
<212> TYPE: DNA
<213> ORGANISM: Homo sapiens

<400> SEQUENCE: 4
atggcgccca ccatccagac ccaggcccag cgggaggatg ccacaggcc caattcccac      60 cggactctgc ctgagaggtc tggagtggtc tgccgagtca agtactgcaa tagcctccct    120
gatatcccct tcgaccccaa gttcatcacc taccccttcg accagaacag gttcgtccag    180
tacaaagcca cttccttgga gaaacagcac aaacatgacc tcctgactga gccagacctg    240
ggggtcacca tcgatctcat caatcctgac acctaccgca tcgaccccaa tgttcttcta    300
gatccagctg atgagaaact tttggaagag agattcagg ccccccaccag ctccaagaga    360 tcccagcagc acgcgaaggt ggtgccatgg atgcgaaaga cagagtacat ctccactgag    420
ttcaaccgtt atggcatctc caatgagaag cctgaggtca gattggggt ttctgtgaag    480 cagcagtta ccgaggaaga aatatacaaa gacagggata gccagatcac agccattgag    540
aagactttgt aggatgccca gaaatcaatc tcacagcatt acagcaaacc ccgagtcaca    600
ccggtggagg tcatgcctgt cttcccagac tttaagatgt ggatcaatcc atgtgctcag    660
gtgatctttg actcagaccc cagccccaag gacacgagtg tgcagctgc gttggagatg    720 atgtctcagg ccatgattag gggcatgatg gatgaggaag ggaaccagtt tgtggcctat    780
ttcctgcctg tagaagagac gttgaagaaa cgaaagcggg accaggagga ggagatggac    840
tatgcaccag atgatgtgta tgactacaaa attgctcggg agtacaactg gaacgtgaag    900
aacaaagcta gcaagggcta tgaggaaaac tacttcttca tcttccgaga gggtgacggg    960
gtttactaca atgagttgga aaccagggtc cgccttagta agcgccgggc caaggctggg   1020
gttcagtcag gcaccaacgc cctgcttgtg gtcaaacatc gggacatgaa tgagaaggaa   1080
ctggaagctc aggaggcacg gaaggcccag ctagaaaacc acgaaccgga ggaggaagag   1140
gaagaggaga tggagacaga agagaaagaa gctgggggct cagatgagga gcaggagaag   1200
ggcagcagca gtgagaagga gggcagtgaa gatgagcact cgggcagcga gagtgaacgg   1260
gaggaaggtg acagggacga ggccagtgac aagagtggca gtggtgagga cgagagcagc   1320
gaggatgagg cccgggctgc ccgtgacaaa gaggagatct ttggcagtga tgctgattct   1380
gaggacgatg ccgactctga tgatgaggac agaggacagg cccaaggtgg cagtgacaat   1440
```

-continued

```
gattcagaca gcggcagcaa tgggggtggc cagcggagcc ggagccacag ccgcagcgcc    1500
agtcccttcc ccagtggcag cgagcactcg gcccaggagg atggcagtga agctgcagct    1560
tctgattcca gtgaagctga tagtgacagt gactga                              1596
```

```
<210> SEQ ID NO 5
<211> LENGTH: 19
<212> TYPE: RNA
<213> ORGANISM: Artificial Sequence
<220> FEATURE:
<223> OTHER INFORMATION: siRNA strand

<400> SEQUENCE: 5
cagguucguc caguacaaa                                                 19
```